(12) United States Patent
Willerton et al.

(10) Patent No.: US 8,140,161 B2
(45) Date of Patent: Mar. 20, 2012

(54) METHOD AND MEDICAL SYSTEM FOR DETERMINING A LINK QUALITY OF A COMMUNICATION LINK IN SUCH A MEDICAL SYSTEM

(75) Inventors: Mark Willerton, Vadstena (SE); Viktor Skoog, Hässelby (SE); Hans Strandberg, Sundbyberg (SE); Lars Forsmark, Bromma (SE)

(73) Assignee: St. Jude Medical AB, Jarfalla (SE)

( * ) Notice: Subject to any disclaimer, the term of this patent is extended or adjusted under 35 U.S.C. 154(b) by 240 days.

(21) Appl. No.: 12/515,341

(22) PCT Filed: Nov. 16, 2006

(86) PCT No.: PCT/SE2006/001308
§ 371 (c)(1),
(2), (4) Date: Jan. 15, 2010

(87) PCT Pub. No.: WO2008/060197
PCT Pub. Date: May 22, 2008

(65) Prior Publication Data
US 2010/0121413 A1    May 13, 2010

(51) Int. Cl.
*A61N 1/00* (2006.01)
(52) U.S. Cl. .......................................... 607/32; 607/27
(58) Field of Classification Search .............. 607/27–32, 607/59, 60
See application file for complete search history.

(56) References Cited

U.S. PATENT DOCUMENTS

| 5,476,488 | A | 12/1995 | Morgan et al. |
| 5,683,432 | A | 11/1997 | Goedeke et al. |
| 5,843,139 | A | 12/1998 | Goedeke et al. |
| 6,647,299 | B2 | 11/2003 | Bourget |
| 2003/0136418 | A1 | 7/2003 | Behm |

FOREIGN PATENT DOCUMENTS

EP        0 850 663  B1    3/2005

*Primary Examiner* — Scott Getzow
(74) *Attorney, Agent, or Firm* — Schiff Hardin LLP

(57) ABSTRACT

In a method and medical system for determining a link quality and a link quality margin of a communication link between a programmer device and an implantable medical device of such a medical system, a link quality monitoring circuit of the programmer or the medical device a present link quality and/or link quality margin at reduced signal power using at least one link quality parameter.

28 Claims, 19 Drawing Sheets

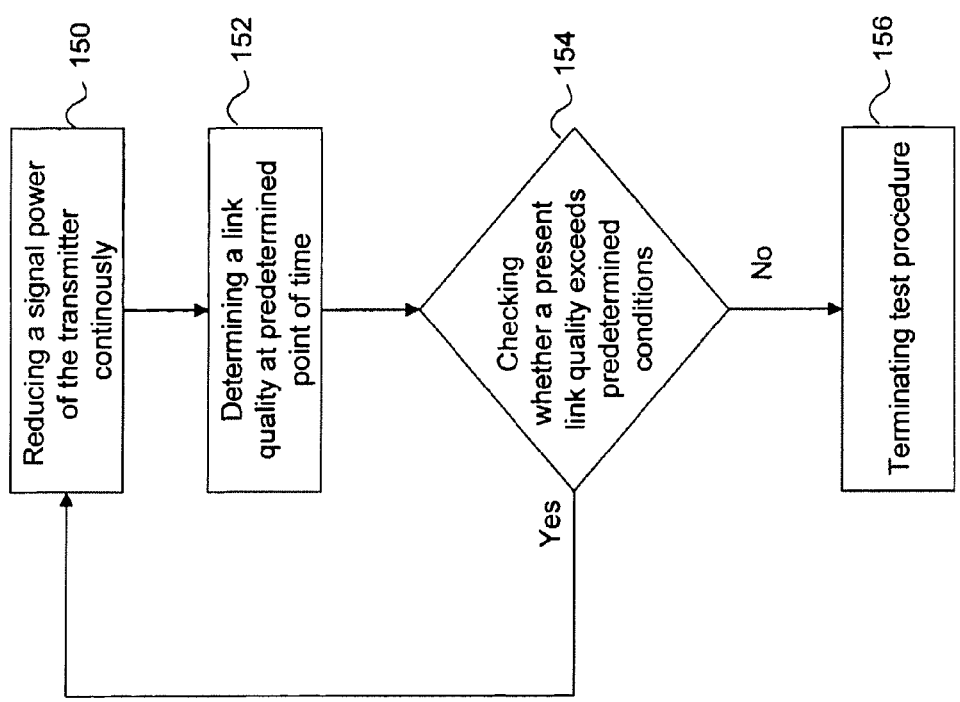

METHOD AND MEDICAL SYSTEM FOR DETERMINING A LINK QUALITY OF A COMMUNICATION LINK IN SUCH A MEDICAL SYSTEM

BACKGROUND OF THE INVENTION

1. Field of the Invention

The present invention generally relates to cardiac pacing systems and, in particular, to methods and medical systems for determining a link quality and a link quality margin of a communication link between a programmer device and an implantable medical device of such a medical system.

2. Description of the Prior Art

Telemetry communication is normally used between an implantable medical device, such as an implantable bi-ventricular pacemaker or a CRT (Cardiac Resynchronization Therapy) device, and an external or programmer workstation to transfer data between the devices, for example, to transfer IEGM data of the heart of the patient from an implanted device to the programmer or to transfer updating data for updating a certain setting of the implanted device from the programmer to the implanted device. In telemetry communications, the operation depends inter alia on used transmission power, interference, reflecting properties in the near environment, the placement of the RF communication unit of the programmer etc. A user of the programmer device and/or the pacemaker needs information of the telemetry performance during such a telemetry communication session, for example, in order to be able to place the RF communication unit at a good position. If the RF communication unit is placed at a bad position, the radio link will be unreliable and it might even break down. Today, the link quality is used to judge whether the RF communication unit is placed at a suitable location with respect to the patient carrying the implanted medical device. The link quality is affected by the separation between the RF communication unit and the implanted medical device and the interference, which may arise from external functions (i.e. external device in the environment) but also from device internal functions (e.g. high voltage charge or shocking). Thus, there would be an advantage if the user of the programmer and/or the implantable medical device were provided with an indication of the link quality.

In U.S. Pat. No. 6,647,299, a solution where a light emitting diode (LED) is used as visible indicator to assist a user to find the desired telemetry location of a programmer for a bi-directional communication link between the programmer and an implantable medical device. Through variations of the visible indicator, the user will know the relative location of the programmer and the implanted device. When the programmer is in the proper telemetry position and the signal strength and accuracy have been confirmed, the light indicator will indicate that a link has been established.

However, a problem with existing link quality indicators is that they are based on the momentary conditions and do not identify whether there is a sufficient link quality margin to cope with a sudden increase in the level of interference. In U.S. Pat. No. 5,843,139 various aspects of system performance in a system including an implantable medical device and a programmer are monitored to determine the momentary performance of the system. The monitored parameters comprises bit-error rate, signal strength, signal-to-noise ratio and the presence of local RF noise and non-telemetry RF-signals.

Therefore, it would be advantageous if a link quality and/or a link quality margin of a communication link between a programmer and an implantable medical device could be continuously monitored during a communication session.

Furthermore, there is a need within the art of an efficient, reliable and simple way of testing the link quality and/or link quality margin of a communication link during a communication session between an implantable medical device, such as a pacemaker, and an external device, such as a programmer workstation.

It is also desirable to provide means for presenting the link quality or the link quality margin for a user, such as a physician, of the programmer device or for a patient in a distinct and intuitive manner.

SUMMARY OF THE INVENTION

Thus, an object of the present invention is to provide methods, medical systems including an external programmer device and an implantable medical device and computer program products for such devices for testing a link quality of a communication link between a programmer and an implantable medical device.

Another object of the present invention is to provide methods, medical systems including an external programmer device and an implantable medical device and computer program products for such devices for determining or calculating a link quality margin of a communication link between a programmer and an implantable medical device.

A further object of the present invention is to provide methods, medical systems including an external programmer device and an implantable medical device and computer program products for such devices for continuously monitoring a link quality and/or a link quality margin of a communication link between a programmer and an implantable medical device to regulate or adjust a signalling power during a communication session.

A further object of the present invention is to provide methods, medical systems including an external programmer device and an implantable medical device and computer program products for such devices for continuously monitoring a link quality and/or a link quality margin of a communication link between a programmer and an implantable medical device to obtain a communication link having a high degree of reliability and a high quality with respect to the data transmission at a low signalling power.

Yet another object of the present invention is to provide methods, medical systems including an external programmer device and an implantable medical device and computer program products for such devices for testing the link quality or link quality margin of a communication link during a communication session between an implantable medical device and an external programmer device in an efficient, reliable and simple way.

These and other objects of the present invention are achieved by means of medical systems and methods for such systems, and computer program products having the features defined in the independent claims. Preferable embodiments of the invention are characterized by the dependent claims.

According to a first aspect of the present invention, there is provided a medical system comprising an external programmer device and an implantable medical device, wherein a link quality monitoring circuit of the programmer is adapted to determine or monitor a link quality of a communication link during a communication session between the programmer and the implantable medical device, the link quality monitoring circuit further being adapted to: instruct a transmitter of a communication unit of the programmer to reduce the signal power from an initial signal power level according to a predetermined signal power adjusting protocol; obtain at least one link quality parameter at a present signal power level from a link quality parameter calculation circuit of the implantable medical device and/or from a link quality parameter calculation circuit of the programmer at predetermined intervals; determine a present link quality using the obtained at least one quality parameter; and instruct the transmitter of the communication unit of the programmer to adjust the reduced signal power based on the present link quality and the signal power adjusting protocol.

In a second aspect of the present invention, there is provided a medical system comprising an external programmer device and an implantable medical device, wherein the link quality monitoring circuit of the programmer is adapted to perform a link quality test to determine a link quality of a communication link during a communication session between the programmer and the implantable medical device. The link quality monitoring circuit is adapted to: instruct a transmitter of a communication unit of the programmer to reduce a signal power from an initial signal power level according to a predetermined test protocol; obtain at least one link quality parameter at reduced signal power from a link quality parameter calculation circuit of the implantable medical device; determine a present link quality at reduced signal power using the obtained at least one link quality parameter; and instruct the transmitter of the communication unit of the programmer to return to the initial signal power level when the link quality test has been finished.

According to a third aspect of the present invention, there is provided a medical system comprising an external programmer device and an implantable medical device, wherein a link quality monitoring circuit of the implantable medical device is adapted to perform a link quality test to determine a link quality of a communication link during a communication session between the programmer and the implantable medical device. The link quality monitoring circuit is adapted to: instruct a transmitter of the implantable medical device to reduce a present signal power from an initial signal power level according to a predetermined test protocol; obtain at least one link quality parameter at reduced signal power from a link quality parameter calculation circuit of the programmer device; determine a present link quality at reduced signal power using the obtained at least one link quality parameter; and instruct the transmitter of the implantable medical device to return to the initial signal power level when the link quality test has been finished.

According to a fourth aspect of the present invention, there is provided a method for determining a link quality in a medical system comprising a programmer device and an implantable medical device. A link quality test is performed to determine a link quality of a communication link during a communication session between the programmer and the implantable medical device including the steps of: reducing a signal power level of a transmitter of a communication unit of the programmer from an initial signal power level according to a predetermined test protocol; obtaining at least one link quality parameter at the implantable medical device at reduced signal power from the implantable medical device; determining a present link quality at reduced signal power using the obtained at least one link quality parameter; and returning to the initial signal power level of the transmitter of the communication unit of the programmer when the link quality test has been finished.

According to a further aspect of the present invention, there is provided a computer program product, directly loadable into an internal memory of an external programmer device, comprising software code portions for causing the external programmer device to perform steps in accordance with the method according to the third aspect.

According to yet another aspect of the present invention, there is provided computer program product, directly loadable into an internal memory of an implantable medical device, comprising software code portions for causing the implantable medical device to perform steps in accordance with the method according to the fourth aspect.

Hence, the invention is based on the idea of continuously monitoring a link quality and/or link quality margin of a communication link between a programmer and an implantable medical device during a communication session and continuously adapt or adjust transmitted power from a sending device, e.g. a transmitter of an RF communication unit of a programmer workstation, during a communication session between the programmer and an implantable medical device using link quality parameters at the programmer and/or the implantable medical device.

Thereby, it is possible to cope with changing transmission conditions and environment during the communication session. The transmitted power can thus be adjusted or adapted to cope with, for example, a sudden increase in the level of interference. Since the signalling power is held at a lowest possible level with respect to the surrounding transmission conditions, the radiated energy can be minimized and, thus, the distances to other programmer workstations located in the proximity of a first workstation can be reduced. That is, using the present invention, a distance between two workstations communicating with an implantable medical device, respectively, can be reduced in comparison with the technique used today, i.e. sending at a constant signal power level.

In one embodiment of the present invention, the signal power is reduced from said present signal power level if said at least one quality parameter satisfies at least a first set of predetermined conditions according to said protocol and the signal power is increased from said present signal power level if said at least one quality parameter satisfies at least a second set of predetermined conditions according to said protocol.

Moreover, the present signal power level can be maintained at a present level if said at least one quality parameter satisfies at least a third set of predetermined conditions and/or the signal power can be increased to an initial signal power level if at least a fourth set of predetermined conditions are satisfied.

Consequently, the power consumption can be reduced the same time as an adequate link quality margin or a link quality satisfying predetermined conditions with respect to, e.g. an error correction of transmitted data or re-transmissions of transmitted data packets, can be maintained during the communication session. In other words, the signalling power is continuously held at a level such that predetermined conditions regarding, for example, error correction of transmitted data and/or re-transmissions of transmitted data packets is satisfied.

According to embodiments of the present invention, a first set of conditions of the protocol includes: the number of error corrected blocks in the implantable medical device (ECCi) being equal to 0 and the number of blocks that could not be corrected in the implantable medical device (CRCi) being equal to 0 for two consecutive intervals or determinations; the second set of conditions of the protocol includes: ECCi being higher than 10 and CRCi being higher than 0 and lower than 40; the third set of conditions of the protocol includes: ECCi being lower than 10 and CRCi being equal to or higher than 0 and lower than 40; and the fourth set of conditions of the protocol includes: CRCi being higher than 40 or at a change of an antenna of the communication device.

According to an aspect of the present invention, there is provided a method for determining a link quality in a medical system comprising an external programmer device and an implantable medical device. A link quality test is performed to determine a link quality of a communication link during a communication session between the programmer device and the implantable medical device, including the steps of: reducing a present signal power of a transmitter of the implantable medical device from an initial signal power level according to a predetermined test protocol; obtaining at least one link quality parameter at reduced signal power from the programmer device; determining a present link quality at reduced signal power using the obtained at least one link quality parameter; and instructing the transmitter of the implantable medical device to return to the initial signal power level when the link quality test has been finished.

The present invention is hence further based on the insight that transmitted power from a sending device, e.g. a transmitter of an RF communication unit of a programmer workstation, has an equivalent effect on link quality of a communication link between the programmer and an implantable medical device as increasing noise or distance. Therefore, by momentarily reducing the transmitter signal power, the effect of increased noise or distance can be simulated or tested and hence measured or determined in an effective and simple manner.

According to one embodiment of the present invention, the link quality parameter calculation circuit may comprise an error detection circuit adapted to detect at least one of the following link quality parameters: forward error correction (FEC), cyclic redundancy check (CRC), or bit error rate (BER).

In a further embodiment of the present invention, the link quality parameter calculation circuit may comprise a signal strength and noise detection circuit adapted to detect at least one of the following link quality parameters: signal strength, or signal-to-noise ratio (SNR).

Furthermore, the link quality parameter calculation circuit may comprise a link delay calculation circuit adapted to calculate a link delay of the communication link using a received response message from the programmer device or by reading a register of a communication unit of the programmer device.

In addition, the link quality parameter calculation circuit may comprise a re-transmission calculation circuit adapted to calculate a number of re-transmissions of at least one data packet sent from the programmer device via the communication link as a link quality parameter.

In an embodiment of the present invention, the link quality monitoring circuit is adapted to: obtain at least one link quality parameter from the signal strength and noise detection circuit of the implantable medical device corresponding to a signal strength at a receiver of the implantable medical device; compare the obtained signal strength of the receiver of the implantable medical device with a predetermined signal strength threshold; and if the signal strength of the receiver is found to exceed the signal strength threshold, determine that the present link quality satisfies predetermined conditions.

According to an embodiment of the present invention, the link quality monitoring circuit may be adapted to initiate the link quality test prior to a transmission of data classified to be critical.

Moreover, the link quality monitoring circuit may be adapted to initiate the link quality test at predetermined intervals during the communication session.

Further, the link quality monitoring circuit is adapted to execute a predetermined number of tests; and determine a link quality using the link qualities of the predetermined number of tests.

In yet another embodiment of the present invention, the programmer device and/or the communication unit of the programmer device comprises presentation means adapted to present the link quality and/or the link quality margin in a visually recognizable way for an operator. For example, the presentation means may comprise at least two light emitting diodes adapted to present the link quality margin in a visually recognizable way for a user of the programmer device and/or communication unit.

Furthermore, the presentation means of the programmer device may comprise a display screen, the control circuit of the programmer device comprising means for generating a graphical user interface on the display screen adapted to present the link quality and/or the link quality margin in a visually recognizable way for a user by means of at least one distinctive colour and at least one distinctive symbol.

In accordance with another embodiment of the present invention, the link quality monitoring circuit of the programmer device is adapted to send a link quality test instruction to a control circuit of the implantable medical circuit instructing the control circuit to determine a link quality of a communication link between the programmer and the implantable medical device, the link quality test instruction further instructing the control circuit to instruct a transmitter of the implantable medical device to reduce a present signal power from an initial signal power level according to a predetermined test protocol; obtain at least one link quality parameter at reduced signal power from a link quality parameter calculation circuit of the programmer; determine a present link quality at reduced signal power using the obtained at least one link quality parameter; and when the link quality test has been finished, send a stop instruction to the control circuit of the implantable medical circuit instructing the control circuit to instruct the transmitter to return to the initial signal power level. Thereby, the link quality and/or link quality margin of the uplink can be determined.

According to embodiments of the present invention, the link quality and/or the link quality margin, and the link quality parameters can also be used to control an antenna switch. An antenna switching process may be started, for example, when the margin is determined to be too low, i.e. when a present link quality is below a predetermined threshold. If there are more than two antennas, each antenna may be activated during a predetermined period of time and the link margin may be determined for each antenna in order to find the antenna having the best receiving conditions.

In a further embodiment of the present invention, the link quality and/or the link quality margin, and the link quality parameters is/are used to evaluate and trigger a change of parameters such as transmitter power, modulation method, etc.

According to a further embodiment of the present invention, in a communication unit of the programmer having two orthogonally arranged antennas, a test is performed when a communication link is established to identify which antenna providing the best transmission conditions, for example, using the monitoring or test procedures according to the different aspects of the invention discussed above. The obtained link quality parameters are also used to trigger a change of antenna and to compare the antennas during a communication session.

As will be apparent to those skilled in the art, steps of the methods of the present invention, as well as preferred embodiment thereof, are suitable to realize as a computer program or a computer readable medium.

The features that characterize the invention, both as to organization and to method of operation, together with further objects and advantages thereof, will be better understood from the following description used in conjunction with the accompanying drawings. It is to be expressly understood that the drawings is for the purpose of illustration and description and is not intended as a definition of the limits of the invention. These and other objects attained, and advantages offered, by the present invention will become more fully apparent as the description that now follows is read in conjunction with the accompanying drawings.

BRIEF DESCRIPTION OF THE DRAWINGS

FIG. 15 is flow chart of the embodiment of the method for determining a link quality and/or link quality margin of a communication link between an implantable medical device and programmer device of a medical system including the test procedure shown in FIG. 14.

DESCRIPTION OF THE PREFERRED EMBODIMENTS

In the following, the present invention will be discussed in the context of medical systems comprising at least an implantable pacemaker such as a bi-ventricular pacemaker, and an external or extracorporeal programmer workstation. However, the present invention may also be implemented in system including other implantable medical devices such as a CRT (Cardiac Resynchronization Therapy) device, or an ICD (Implantable Cardioverter Defibrillator).

Figure 1A:
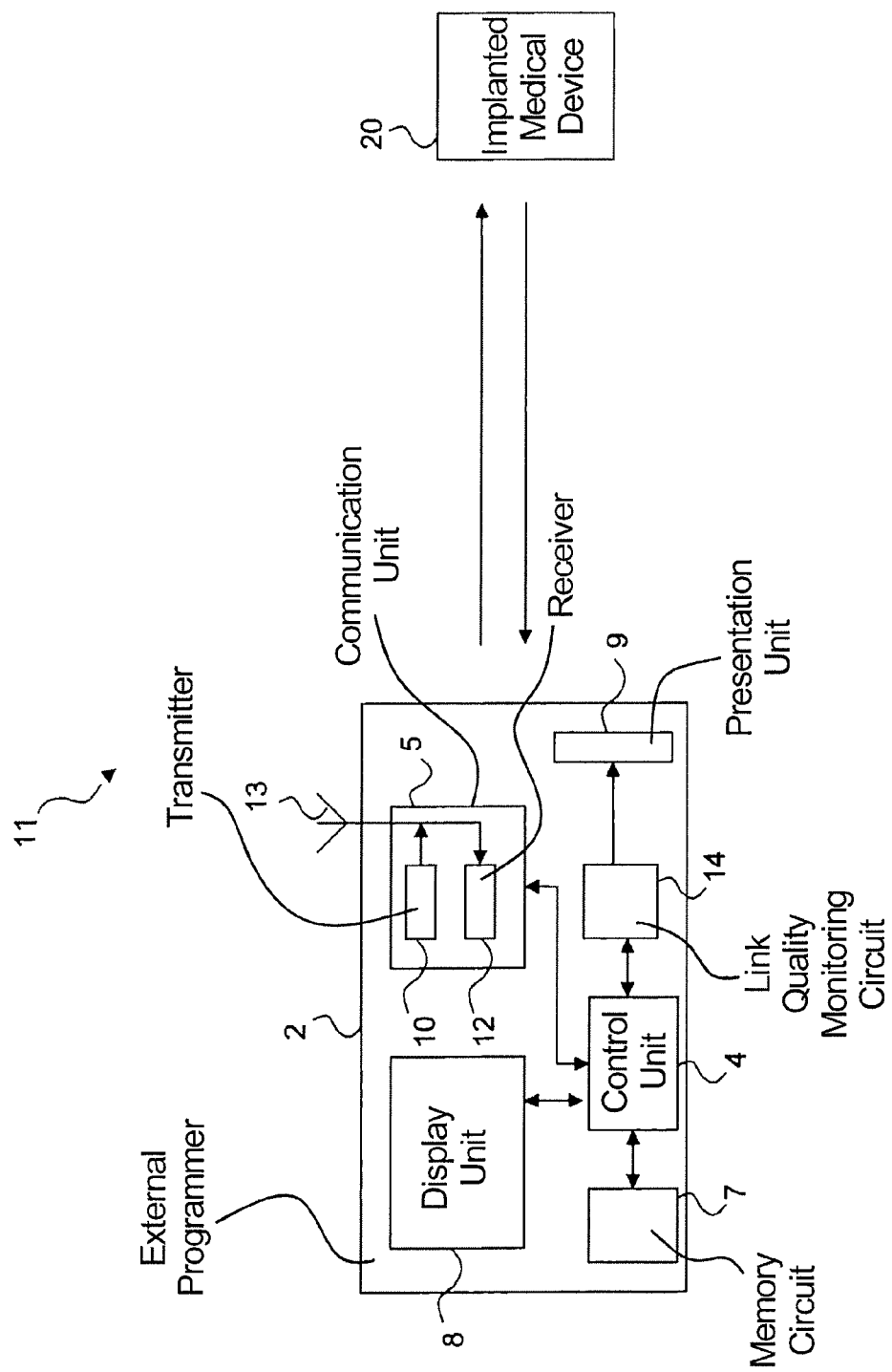
FIG. 1a schematically shows a programmer device and medical system according to an embodiment of the present invention.
Figure 1B:
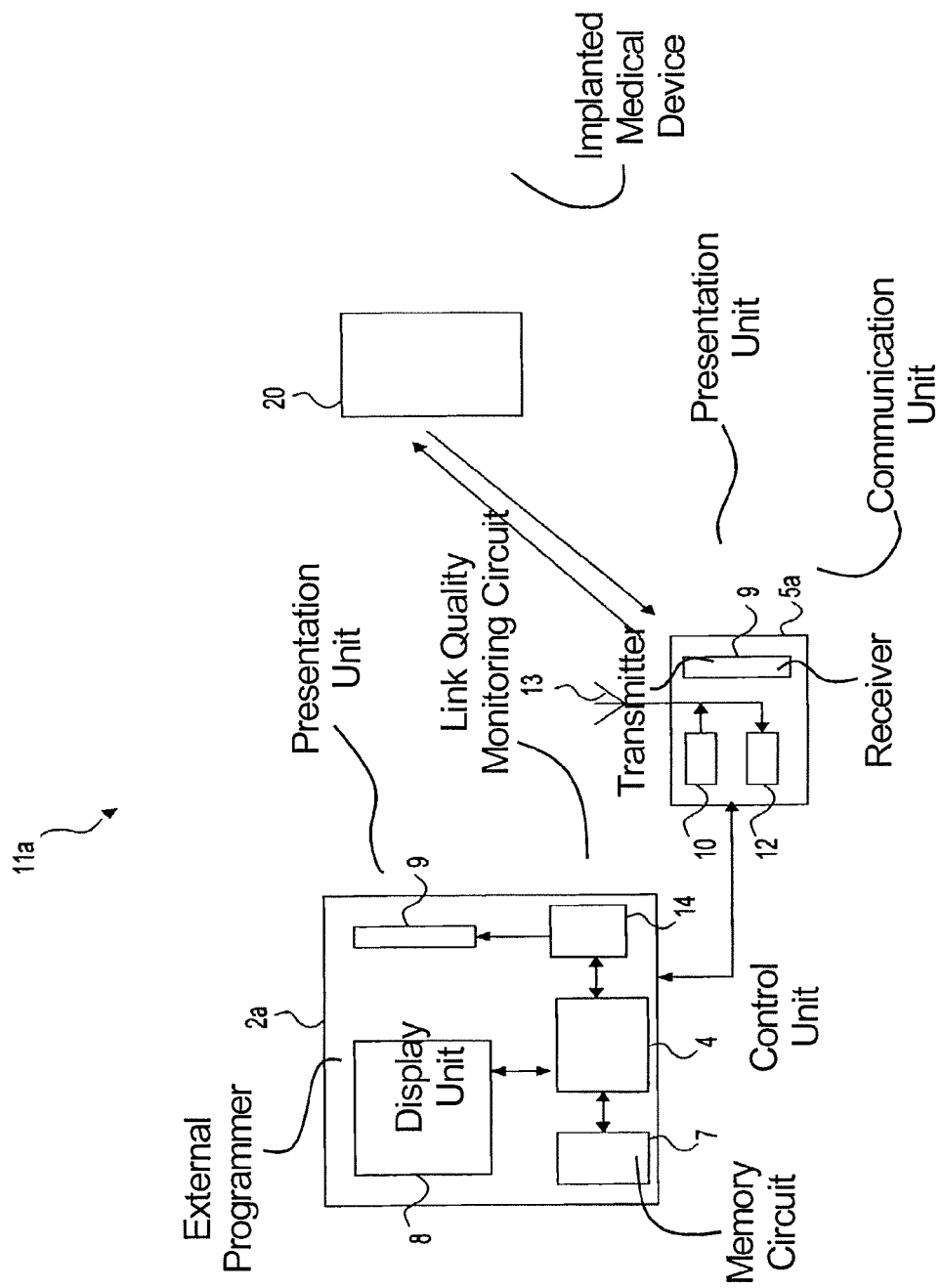
FIG. 1b schematically shows a programmer device and medical system according to another embodiment of the present invention.
Figure 1C:
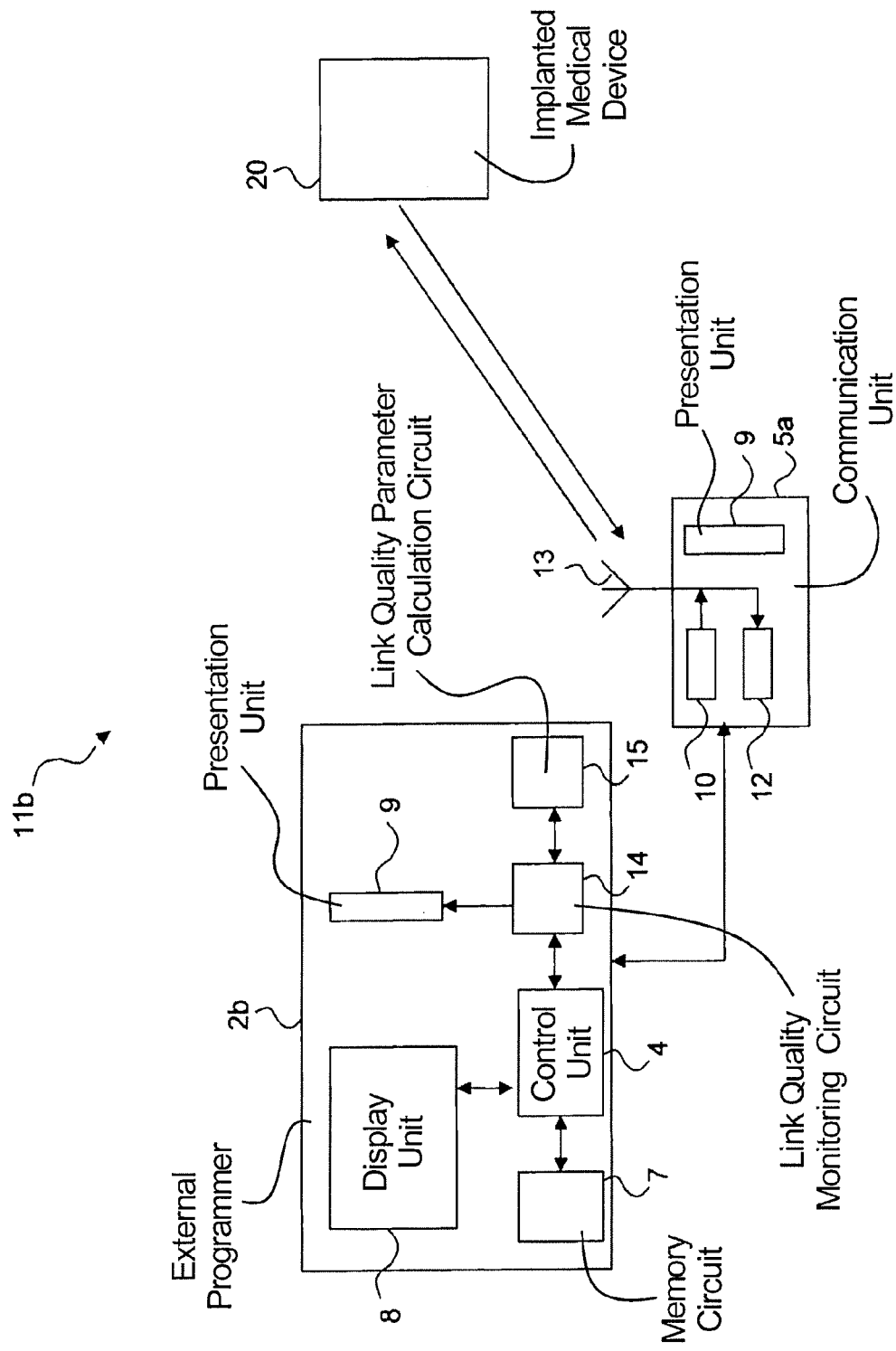
FIG. 1c schematically shows a programmer device and medical system according to a further embodiment of the present invention.
Figure 1D:
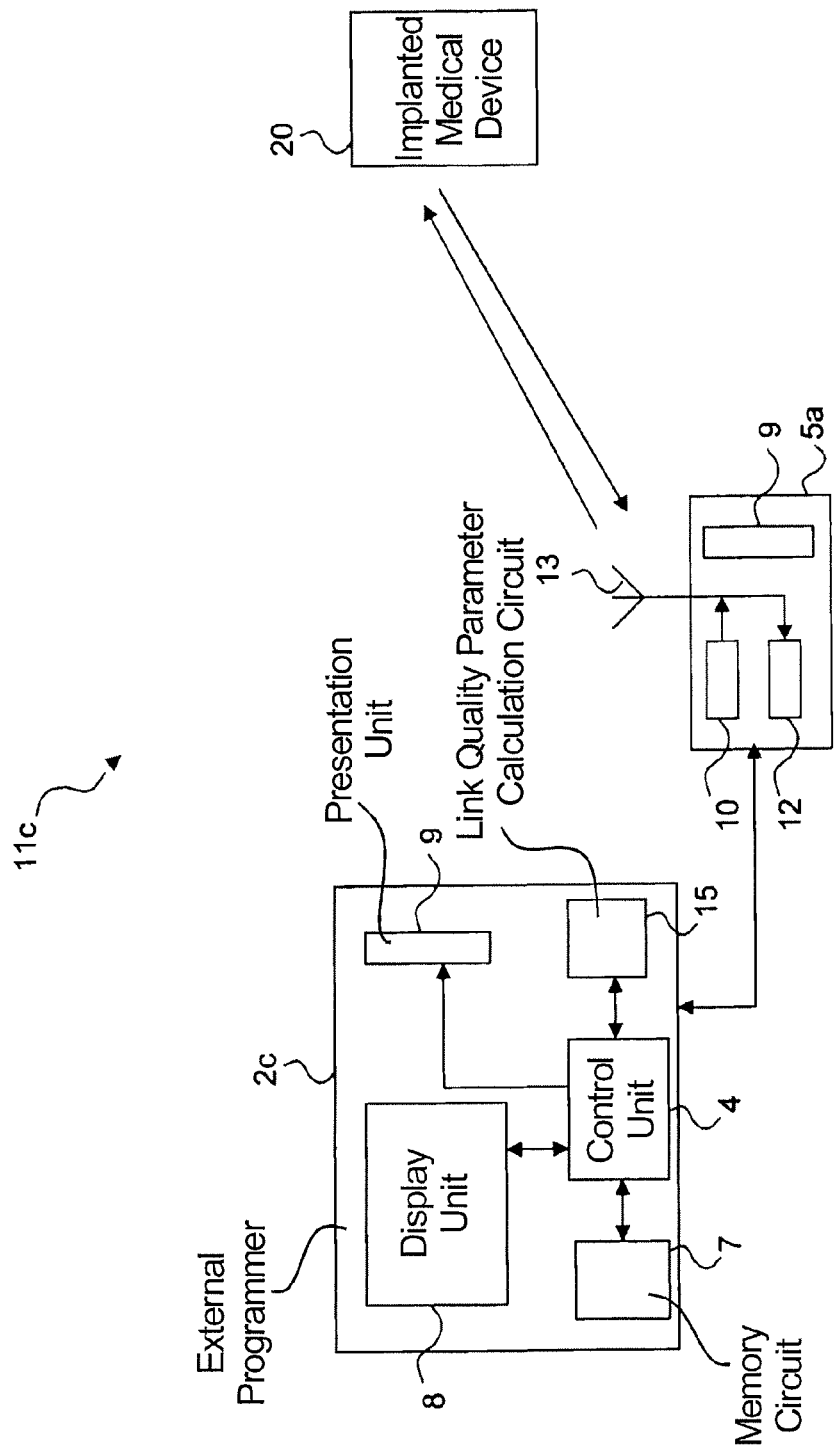
FIG. 1d schematically shows a programmer device and medical system according to yet another embodiment of the present invention.

With reference first to FIGS. 1a-1d, embodiments of the medical system of the present invention will be described. The medical system 11 comprises a programmer workstation 2 and an implanted medical device 20 or 20a (which will be described in more detail with reference to FIGS. 3a and 3b) implanted in a patient (not shown). The programmer 2 includes a control unit 4 comprising a microprocessor and a communication unit 5, e.g. an RF telemetry circuitry for providing bi-directional RF communications with, for example, the implanted medical device 20 or 20a (only implantable medical device 20 shown in FIGS. 1a-1d, but, as the skilled man realize, the implantable medical device 20a may also be used in the system), which communication unit 5 includes a transmitter 10, a receiver 12 and an antenna 13. The programmer 2 may download data, commands or instructions to the implanted medical device 20 and may receive data, commands or instructions via uplink from the implanted medical device 20. The communication unit 5 may be integrated in the programmer device 2, or, as shown in FIGS. 1b, 1c and 1d, as a separate unit connected to the programmer device via, for example, an USB connection or adapted to communicate with the programmer device 2a, 2b, or 2c wirelessly by means of a number of different technologies including short range communication links including BLUETOOTH, and IEEE 802.11b, or other types of short-range wireless connections such as Infrared.

Further, the programmer 2 comprises a link quality monitoring circuit 14 adapted to continuously monitor a link quality of a communication link or to perform, for example, a link quality test to determine a link quality and/or a link quality margin of a communication link between the programmer 2 and the implantable medical device 20. In one embodiment, the link quality monitoring circuit 14 is integrated in the control unit 4. In one embodiment of the present invention, the link quality monitoring circuit 14 is adapted to perform a link quality test to determine a link quality of a communication link during a communication session between the programmer device 2 and the implantable medical device 20. In one alternative embodiment, the test is initiated prior to a transmission of data determined to be critical, i.e. after the communication link has been established and at the beginning of the communication session. According to another embodiment, the test is performed at periodic intervals during normal communication.

The programmer 2 also comprises a memory circuit 7 which may include a random access memory (RAM) and/or a non-volatile memory such as a read-only memory (ROM). The memory circuit may store, for example, a signal power adjusting protocol or a test protocol, a display unit or monitor 8 for presenting information for a user by means of a graphical user interface (GUI) such as an indication of a link quality or a link quality margin, and input devices (not shown), for example, a keyboard and a mouse, which enable a user to, for example, input information and commands.

Moreover, the programmer 2 (and/or the communication unit 5, see FIGS. 1b and 1b) includes a presentation unit 9 adapted to present or indicate, for example, a link quality or a link quality margin of a communication link between the programmer 2 and the implantable medical device 20 for a user. According to an embodiment, the presentation unit 9 includes five LED (light emitting diodes) and in another embodiment a dual colour LED, which will be discussed in more detail below.

Referring now to FIGS. 1b, 1c and 1d, further embodiments of the medical system according to the present invention will be discussed. Like parts in the system shown in FIG. 1a and FIGS. 1b, 1c and 1d will be denoted with the same reference numerals and descriptions thereof will be omitted since they have been described above with reference to FIG. 1a. In the system 11a shown in FIG. 1b, the communication unit 5a is arranged externally from the programmer device 2a and are provided with presentation circuits 9. The communication unit 5a may communicate with the programmer device 2a via a physical connection such as, for example, an USB connection or wirelessly by means of a number of different technologies including short-range communication links including BLUETOOTH, and IEEE 802.11b, or other types of short-range wireless connections such as Infrared.

The system 11b shown in FIG. 1c, the programmer device 2b comprises, in addition to the link quality monitoring circuit 14, a link quality parameter calculation circuit 15 adapted to calculate or determine link quality parameters during a link quality test, which link quality parameter calculation circuit 15 will be discussed in more detail with reference to FIG. 2.

The system 11c shown in FIG. 1d, the programmer device 2c comprises the link quality parameter calculation circuit 15 adapted to calculate or determine link quality parameters during a link quality test, which link quality parameter calculation circuit 15 will be discussed in more detail with reference to FIG. 2.

As those skilled in the art will realize, there are a number of alternative embodiments of the system that are conceivable, for example, the communication unit may be integrated in the programmer comprising the link quality parameter calculation circuit shown in FIG. 1c.

Figure 2:
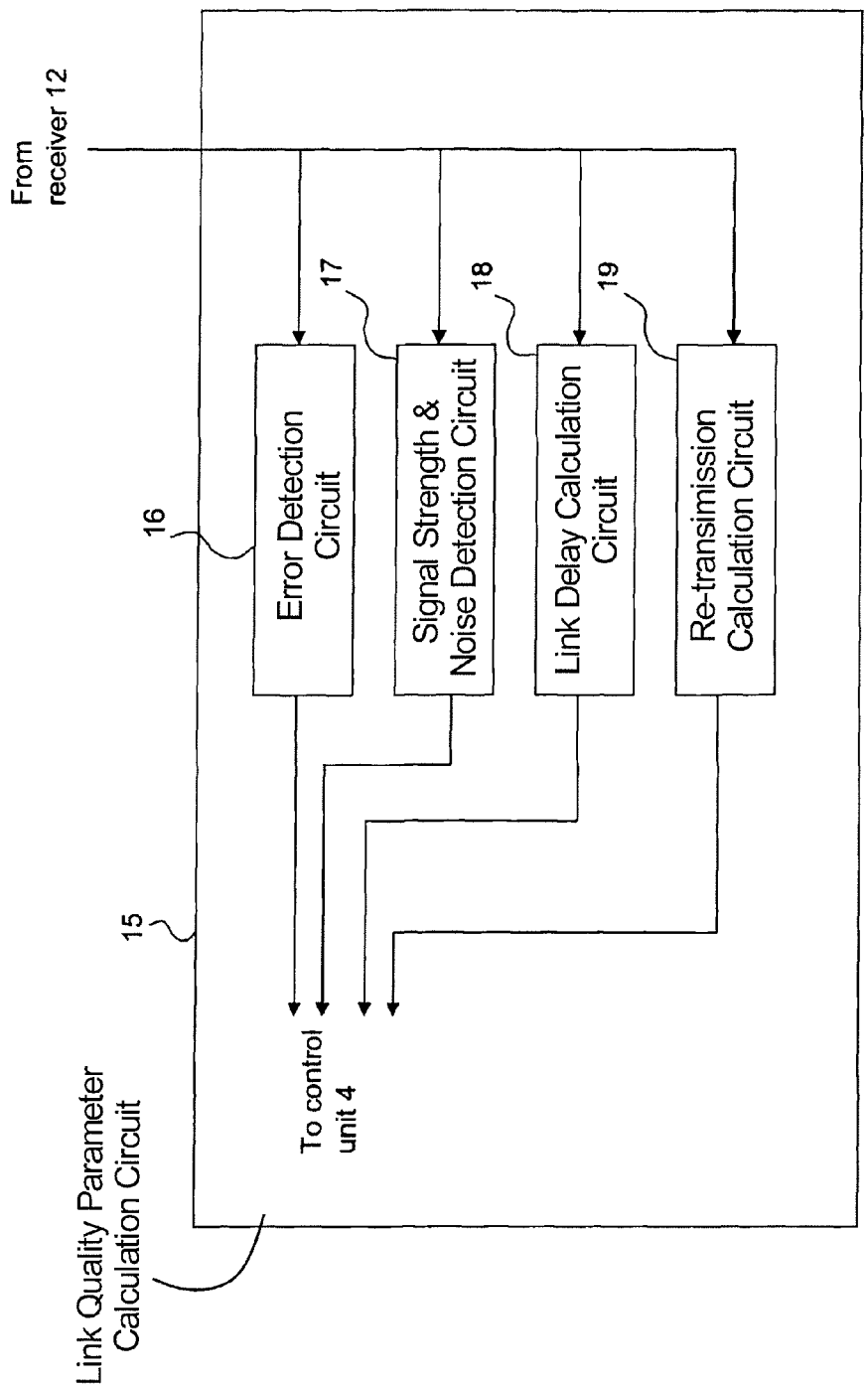
FIG. 2 schematically shows an embodiment of a link quality parameter calculating circuit of a programmer device in accordance with the present invention.

Turning now to FIG. 2, an embodiment of the link quality parameter calculation circuit 15 will be discussed in more detail. In one embodiment, the link quality parameter calculation circuit 15 comprises an error detection circuit 16 adapted to detect at least one of the following link quality parameters: forward error correction (FEC), cyclic redundancy check (CRC), or bit error rate (BER). The error detection circuit 16 is connected to the receiver 12 and the control unit 4 and may utilize well-known error detection techniques to determine, for example, the bit error rate of information received by receiver 12. Further, the error detection circuit 16 may be adapted to sample, e.g. every 100 ms, corrected errors in communication unit 5, 5a and/or detected uncorrectable errors from the communication unit 5, 5a.

Furthermore, the link quality parameter calculation circuit 15 includes a signal strength and noise detection circuit 17 adapted to detect a signal strength and/or a signal-to-noise ratio (SNR) connected to the to the receiver 15 and the control unit 4 and may comprise a logarithmic amplifier which detects and filters the received RF signal and provide a received signal strength indicator that gives a voltage proportional to the logarithm of the signal strength at the receiver 12. Likewise, the noise can be measured under a known period of time during which no received transmission. In this way the signal-to-noise ratio of the received signal can be measure by simple comparison of the signal and noise samples.

Moreover, the link quality calculation circuit 15 may include a link delay calculation circuit 18 adapted to measure or calculate a link delay of the communication link. This delay can be measured by transmitting a message using the ordinary protocol from the transmitter 10 of the communication unit 5, 5a and measure the elapsed time until the response from the implanted medical device 20 has been received. Another way of measuring the link delay is to measure the time required to read a register in the communication unit (see FIGS. 3a and 3b) of the implantable medical device 20. In this case, the measure link delay will not include the buffering times and the delay in the processor of the implantable medical device 20.

The link quality parameter calculation circuit 15 may also comprise a re-transmission calculation circuit 19 adapted to record or count a number of occasions a data packet or message has been retransmitted from the transmitter 10 of the communication unit 5, 5a at predetermined intervals. In one embodiment, the number of occasions a data packet or message has been retransmitted from the transmitter 10 of the communication unit 5, 5a more than a preset times, e.g. 10, is recorded at predetermined intervals, for example, every 100 ms.

As those skilled in the art will realize, the link quality parameter calculation circuit 15 may include one or more or all of the following circuits: an error detection circuit, a signal strength and noise detection circuit, a link delay calculation circuit, and/or a re-transmission calculation circuit. Moreover, there are other conceivable parameters that can be monitored and used for the determination of the link quality and/or link quality margin, for example, the presence of local RF-noise and non-telemetry signals.

Figure 3A:
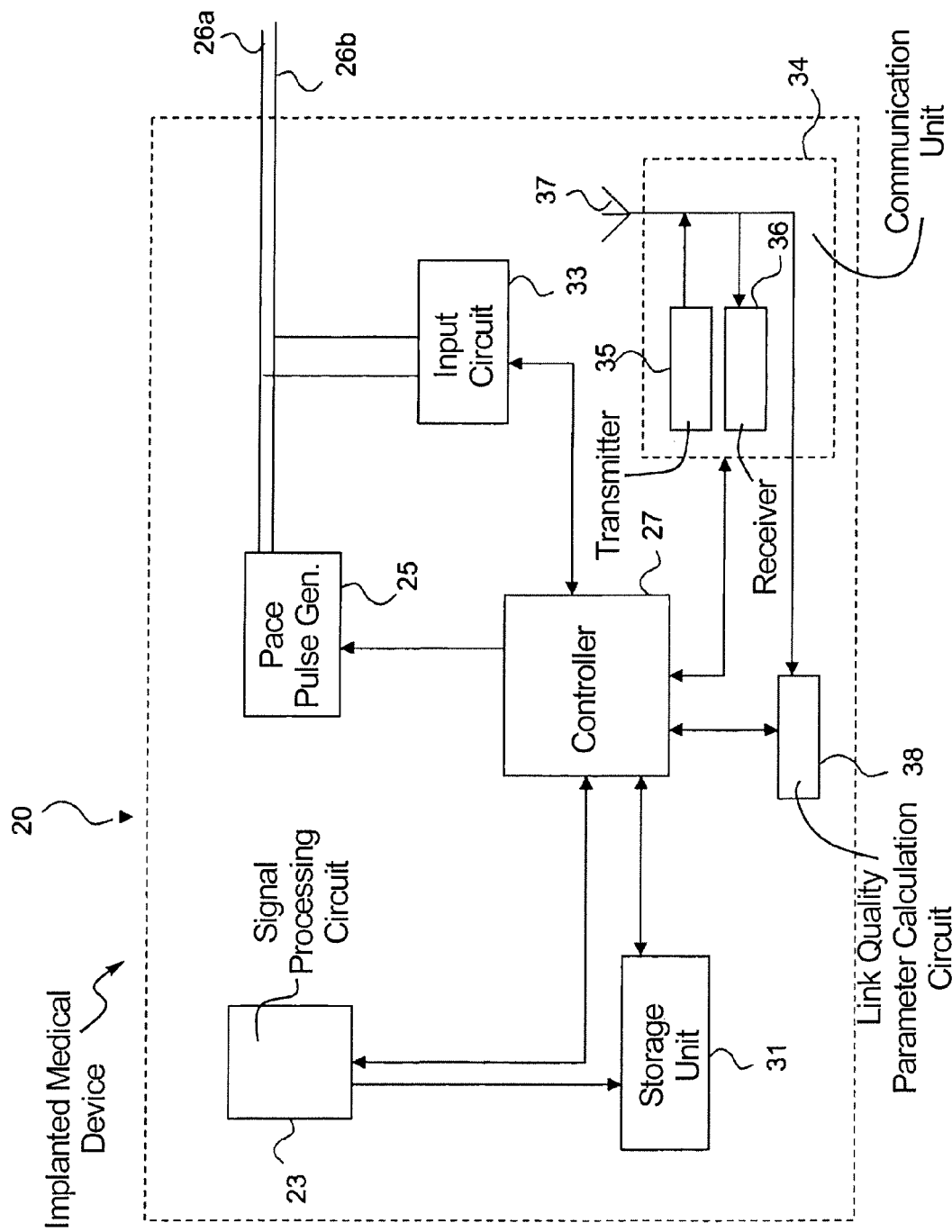
FIG. 3a schematically shows an embodiment of an implantable medical device in accordance with the present invention.
Figure 3B:
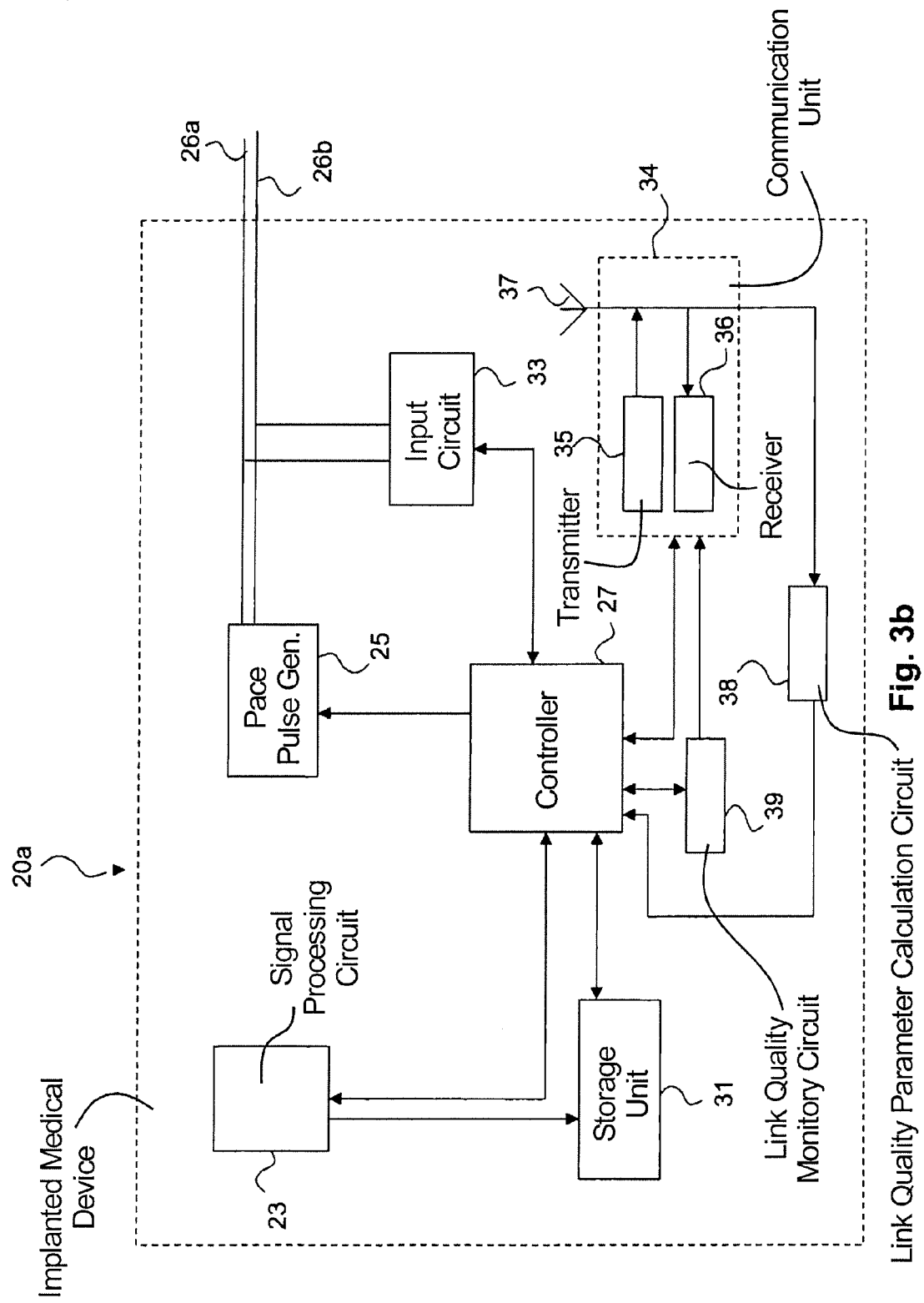
FIG. 3b schematically shows another embodiment of an implantable medical device in accordance with the present invention.

In FIG. 3a, one embodiment of the implantable medical device according to the present invention is shown. The implantable medical device 20, such as a bi-ventricular pacemaker, comprises a housing (not shown) being hermetically sealed and biologically inert. Normally, the housing is conductive and may, thus, serve as an electrode. The pacemaker 20 is connectable to one or more pacemaker leads, where only two are shown in FIGS. 3a and 3b; namely a ventricular lead 26a implanted in the right ventricle of the heart (not shown) and one lead 26b implanted in a coronary vein of the left side of the heart (not shown). The leads 26a and 26b can be electrically coupled to the pacemaker 20 in a conventional manner. The leads 26a, 26b comprises one or more electrodes, such as a tip electrode or a ring electrode, arranged to, inter alia, measure the impedance or transmit pacing pulses for causing depolarization of cardiac tissue adjacent to the electrode (-s) generated by a pace pulse generator 25 under influence of a controller or control circuit 27 including a microprocessor. The controller 27 controls, inter alia, pace pulse parameters such as output voltage and pulse duration.

Furthermore, the implantable medical device 20 comprises at least one sensor (not shown) adapted to sense at least one sensor signal associated with a physiological parameter of the patient. In one embodiment, the sensor is an activity level sensor adapted to sense an activity level of the patient, for example, an accelerometer. The sensor is connected to a signal processing circuit 23 adapted to process sensed signals received from the sensor.

Moreover, a storage unit 31 is connected to the controller 27, which storage unit 31 may include a random access memory (RAM) and/or a non-volatile memory such as a read-only memory (ROM). Storage means 31 is connected to the controller 27 and the signal processing circuit 23. Detected signals from the patient's heart are processed in an input circuit 33 and are forwarded to the controller 27 for use in logic timing determination in known manner. The implantable medical device 20 is powered by a battery (not shown), which supplies electrical power to all electrical active components of the implantable medical device 20. The implantable medical device 20 further comprises a communication unit 34, for example, an RF telemetry circuitry for providing RF communications including a transmitter 35 and a receiver 36 connected to an antenna 37. Thereby, for example, data contained in the storage means 31 can be transferred to the programmer device 2, 2a, 2b, or 2c (see FIGS. 1a-1d) via the communication unit 34 and a programmer interface (not shown) for use in analyzing system conditions, patient information, etc. Moreover, the implantable medical device 20 comprises a link quality parameter calculation circuit 38 adapted to calculate or determine link quality parameters during a link quality test, which link quality parameter calculation circuit 38 will be discussed in more detail with reference to FIG. 4.

Referring to FIG. 3b, a further embodiment of the implantable medical device will be discussed. Like parts in the implantable medical device shown in FIG. 3a and FIG. 3b will be denoted with the same reference numerals and descriptions thereof will be omitted since they have been described above with reference to FIG. 3a. The implantable medical device 20a comprises a link quality monitoring circuit 39 adapted to perform, for example, a link quality test to determine a link quality and/or a link quality margin of a communication link between the programmer 2 and the implantable medical device 20a. In one embodiment, the link quality monitoring circuit 39 is integrated in the controller 27. In one embodiment of the present invention, the link quality monitoring circuit 39 is adapted to perform a link quality test to determine a link quality of a communication link during a communication session between the programmer device 2 and the implantable medical device 20a. In one alternative embodiment, the test is initiated prior to a transmission of data determined to be critical, i.e. after the communication link has been established and at the beginning of the communication session. According to another embodiment, the test is performed at periodic intervals during normal communication.

The link quality monitoring circuit 39 may be adapted to monitor a link quality or perform a link quality test to determine a link quality of a communication link during a communication session between the programmer device 2b or 2c and the implantable medical device 20a.

Figure 4:
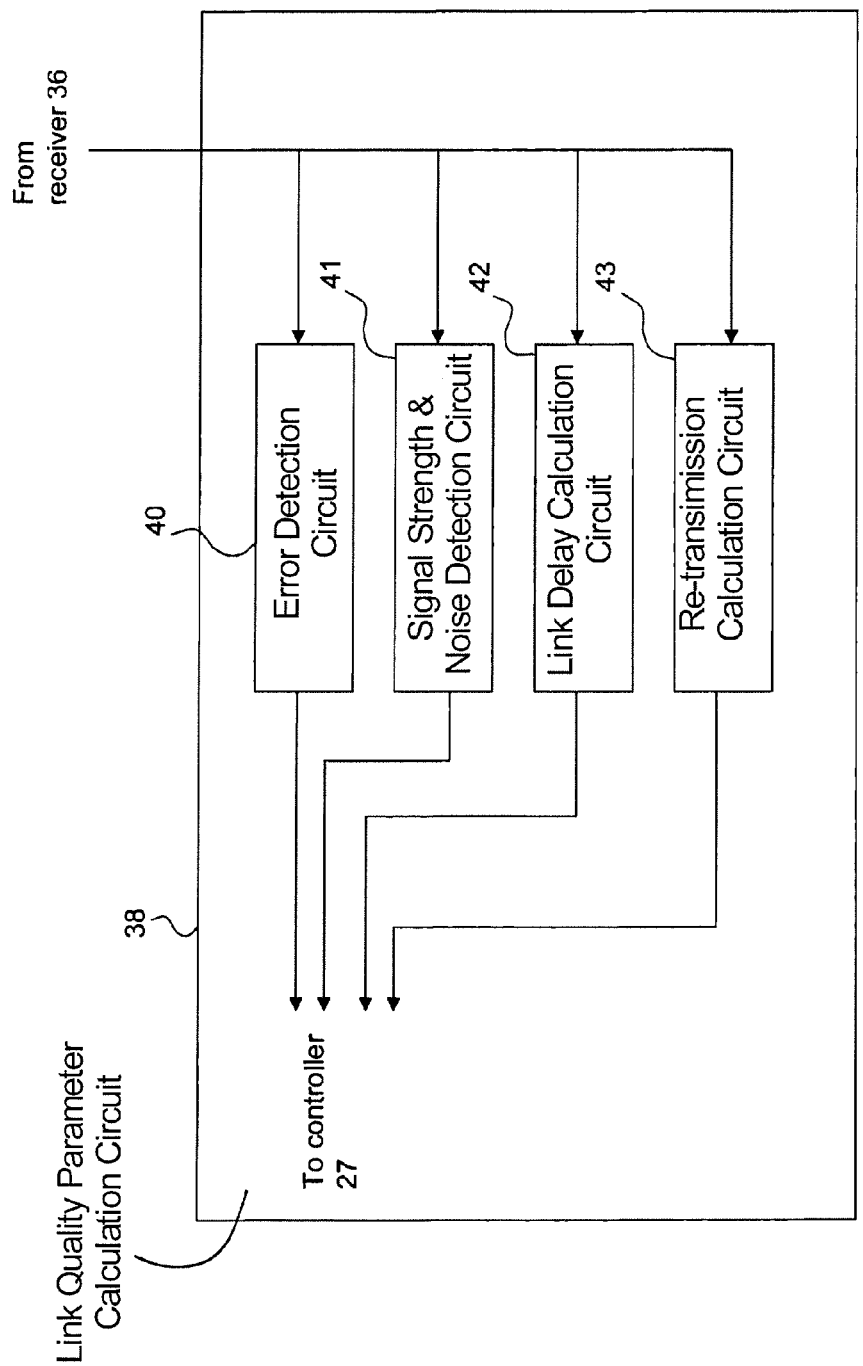
FIG. 4 schematically shows an embodiment of a link quality parameter calculating circuit of an implantable medical device in accordance with the present invention.

Turning now to FIG. 4, an embodiment of the link quality parameter calculation circuit 38 will be discussed in more detail. In one embodiment, the link quality parameter calculation circuit 38 comprises an error detection circuit 40 adapted to detect at least one of the following link quality parameters: forward error correction (FEC), cyclic redundancy check (CRC), or bit error rate (BER). The error detection circuit 40 is connected to the receiver 36 and the controller 27 and may utilize well-known error detection techniques to determine, for example, the bit error rate of information received by receiver 36. Further, the error detection circuit 40 may be adapted to sample, e.g. every 200 ms, corrected errors in communication unit 34 and/or detected uncorrectable errors from the communication unit 34.

Furthermore, link quality parameter calculation circuit 38 includes a signal strength and noise detection circuit 41 adapted to detect a signal strength and/or a signal-to-noise ratio (SNR) connected to the to the receiver 36 and the controller 27 and may comprise a logarithmic amplifier which detects and filters the received RF signal and provide a received signal strength indicator that gives a voltage proportional to the logarithm of the signal strength at the receiver 36. Likewise, the noise can be measured under a known period of time during which no received transmission. In this way the signal-to-noise ratio of the received signal can be measure by simple comparison of the signal and noise samples.

Moreover, the link quality calculation circuit 38 may include a link delay calculation circuit 42 adapted to measure or calculate a link delay of the communication link. This delay can be measured by transmitting a message using the ordinary protocol from the transmitter 35 of the communication unit 34 and measure the elapsed time until the response from the programmer device 2 has been received. Another way of measuring the link delay is to measure the time required to read a register in the communication unit 5, 5a (see FIGS. 1a-1d) of the programmer device 2, 2a, 2c, or 2c. In this case, the measure link delay will not include the buffering times and the delay in the processor of the control unit 4 of the programmer device 2.

The link quality parameter calculation circuit 38 may also comprise a re-transmission calculation circuit 43 adapted to record or count a number of occasions a data packet or message has been retransmitted from the transmitter 35 of the communication unit 34 at predetermined intervals. In one embodiment, the number of occasions a data packet or message has been retransmitted from the transmitter 35 of the communication unit 34 more than a preset times, e.g. 10, is recorded at predetermined intervals, for example, every 100 ms.

As the skilled person realizes, the link quality parameter calculation circuit 38 may include one or more or all of the following circuits: an error detection circuit, a signal strength and noise detection circuit, a link delay calculation circuit, and/or a re-transmission calculation circuit. Moreover, there are other conceivable parameters that can be monitored and used for the determination of the link quality and/or link quality margin, for example, the presence of local RF-noise and non-telemetry signals.

Figure 5:
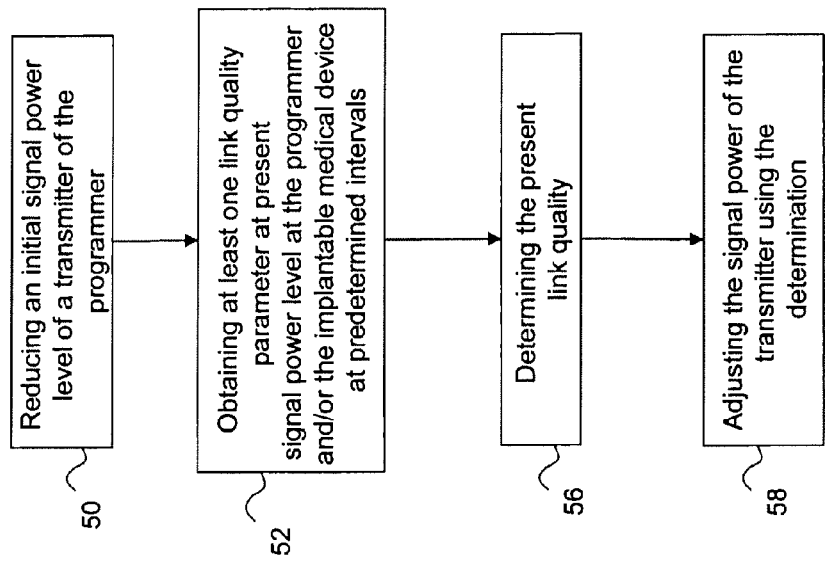
FIG. 5 is a high-level description of the steps of an embodiment of the method for continuously monitoring a link quality and/or link quality margin of a communication link between an implantable medical device and programmer device of a medical system.

Referring now to FIG. 5, a high-level description of the steps of an embodiment of the method for monitoring a link quality and/or link quality margin of a communication link between an implantable medical device and programmer device of a medical system will be given. According to an embodiment, the programmer 2b or the link quality monitoring circuit 14, initiates the monitoring procedure and determines the link quality and/or link quality margin of the communication link between the programmer device 2b and the implantable medical device 20. First, at step 50, the signal power of the transmitter 10 is reduced from an initial signal power according to a signal power adjusting protocol, e.g. a predetermined step, which may be stored in the memory circuit 7 of the programmer 2b. Then, at step 52, at least one link quality parameter at a present signal power level is obtained from a link quality parameter calculation circuit 38 of the implantable medical device 20 and/or from a link quality parameter calculation circuit 15 of the programmer 2b. This at least one link quality parameter may be obtained at predetermined intervals. In one embodiment, the link quality parameters are measured five times per second in the communication unit 5a and ten times per second in the implantable medical device 20. In another embodiment, the link quality parameters are measured ten times per second in the communication unit 5a and ten times per second in the implantable medical device 20. According to embodiments, at least one of the following parameters are obtained: error correction codes (ECC), forward error correction (FEC), cyclic redundancy check (CRC), bit error rate (BER), signal strength, or signal-to-noise ratio (SNR), a link delay of the communication link, a number of re-transmissions of at least one data packet. Thereafter, at step 54, a present link quality using the obtained at least one quality parameter is determined, for example, at predetermined intervals, e.g. five times per second, in the link monitoring circuit 14. In one embodiment, the link quality is determined by using the following parameters: the number of error corrected blocks (ECC) in the implantable medical device 20, the number of block that could not be corrected (CRC) in the implantable medical device 20. Subsequently, at step 56, the transmitter 10 of the communication unit 5a of the programmer 2b is instructed to adjust the present signal power based on the determined present link quality and the protocol, which will be discussed in more detail below with reference to FIG. 6.

Figure 6:
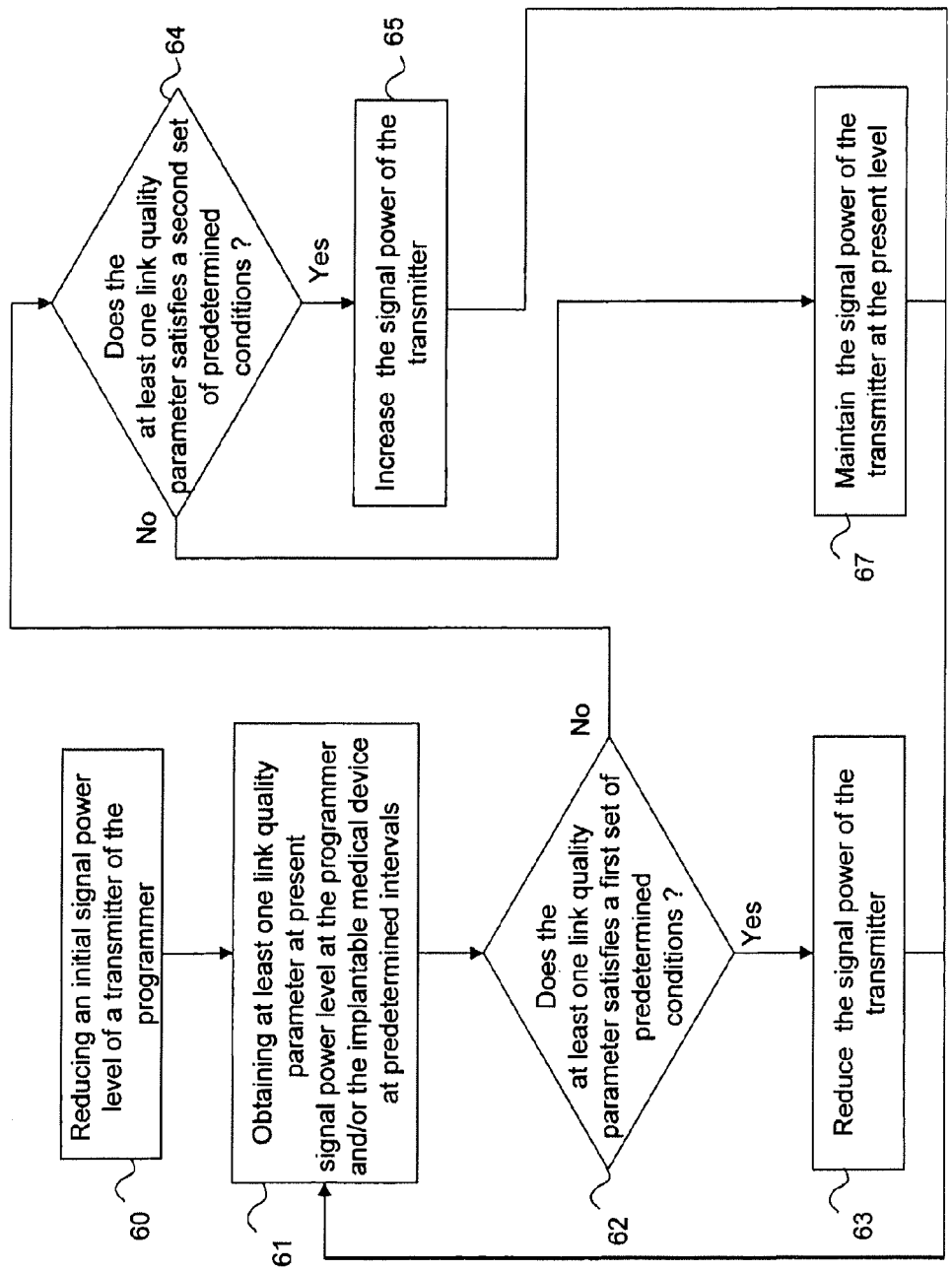
FIG. 6 is a more detailed flow chart illustrating steps of the method for monitoring a link quality and/or link quality margin of a communication link between an implantable medical device and programmer device of a medical system according to the embodiment shown in FIG. 5.

With reference now to FIG. 6, the method for monitoring a link quality and/or link quality margin of a communication link between an implantable medical device and programmer device of a medical system according to an embodiment will be discussed in detail. First, at step 60, the signal power of the transmitter 10 is reduced from an initial signal power according to the signal power adjusting protocol. Then, at step 61, at least one link quality parameter at a present signal power level is obtained from a link quality parameter calculation circuit 38 of the implantable medical device 20 and/or from a link quality parameter calculation circuit 15 of the programmer 2b. This at least one link quality parameter may be obtained at predetermined intervals and in this embodiment the parameters: the number of error corrected blocks (ECC) in the implantable medical device 20 (hereinafter referred to as ECCi), and the number of block that could not be corrected (CRC) in the implantable medical device 20 (hereinafter referred to as CRCi) are obtained. Thereafter, at step 62, it is checked whether ECCi and CRCi, respectively, satisfy a first set of conditions, which in this embodiment are ECCi=0 and CRCi=0 for two consecutive intervals or determinations. If yes, the algorithm proceeds to step 63, where the transmitter 10 of the programmer is instructed to reduce the transmitted signal power one step. The step size is determined by, inter alia, the signal power adjusting protocol, and the present signal power of the transmitter 10. The reduction of the signal power is defined in the adjusting protocol and may be performed in uniform steps or according to successive decreasing steps, i.e. the lower the signal power becomes, the smaller the steps will be. On the other hand, if no, the algorithm proceeds to step 64, where it is checked whether ECCi and CRCi satisfies a second set of conditions, which in this embodiment are ECCi>10 and 0<CRCi<=40. If yes, the algorithm proceeds to step 65, where the transmitter 10 of the programmer is instructed to increase the transmitted signal power one step. In one embodiment, the signal power is increased to the preceding higher signal power level according to the adjusting protocol. However, if it is found that the second set of conditions were not satisfied, for example, if 0<ECCi<10 and CRCi=0 or 0<CRCi<=40, the algorithm proceeds to step 67, where the signal power is maintained at the present level.

In a further embodiment of the present invention, the signal power of the transmitter is increased or returned to the initial or maximum power if a fourth set of predetermined conditions are satisfied, which in this embodiment is at an antenna switch or when CRCi>40.

Figure 7:
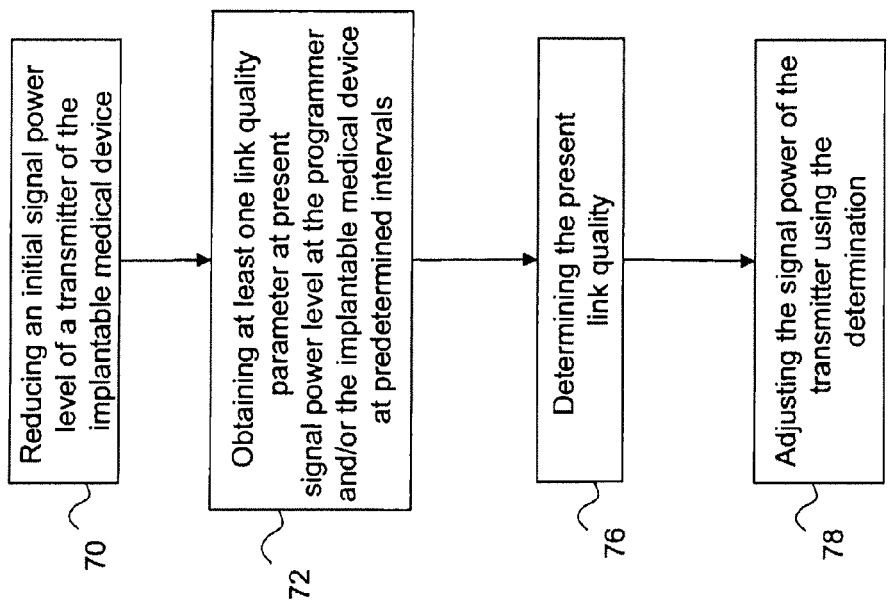
FIG. 7 is a high-level description of the steps of another embodiment of the method for continuously monitoring a link quality and/or link quality margin of a communication link between an implantable medical device and programmer device of a medical system.

Referring now to FIG. 7, a high-level description of the steps of another embodiment of the method for monitoring a link quality and/or link quality margin of a communication link between an implantable medical device and programmer device of a medical system will be given. According to this embodiment, the implantable medical device 20a or the link quality monitoring circuit 39, initiates the monitoring procedure and determines the link quality and/or link quality margin of the communication link between the programmer device 2b, 2c and the implantable medical device 20a. First, at step 70, the signal power of the transmitter 35 is reduced from an initial signal power according to a signal power adjusting protocol, e.g. a predetermined step, which may be stored in the storage means 31 of the implantable medical device 20a. Then, at step 72, at least one link quality parameter at a present signal power level is obtained from a link quality parameter calculation circuit 38 of the implantable medical device 20a and/or from a link quality parameter calculation circuit 15 of the programmer 2b, 2c. This at least one link quality parameter may be obtained at predetermined intervals. In one embodiment, the link quality parameters are measured five times per second in the communication unit 5a and ten times per second in the implantable medical device 20a. In another embodiment, the link quality parameters are measured ten times per second in the communication unit 5a and ten times per second in the implantable medical device 20a. According to embodiments, at least one of the following parameters are obtained: error correction codes (ECC), forward error correction (FEC), cyclic redundancy check (CRC), bit error rate (BER), signal strength, or signal-to-noise ratio (SNR), a link delay of the communication link, a number of re-transmissions of at least one data packet. Thereafter, at step 74, a present link quality using the obtained at least one quality parameter is determined, for example, at predetermined intervals, e.g. five times per second, in the link monitoring circuit 39. In one embodiment, the link quality is determined by using the following parameters: the number of error corrected blocks (ECC) in the implantable medical device 20a, the number of block that could not be corrected (CRC) in the implantable medical device 20a and/or in the programmer 2b, 2c. Subsequently, at step 76, the transmitter 35 is instructed to adjust the present signal power based on the determined present link quality and the protocol, which will be discussed in more detail below with reference to FIG. 8.

Figure 8:
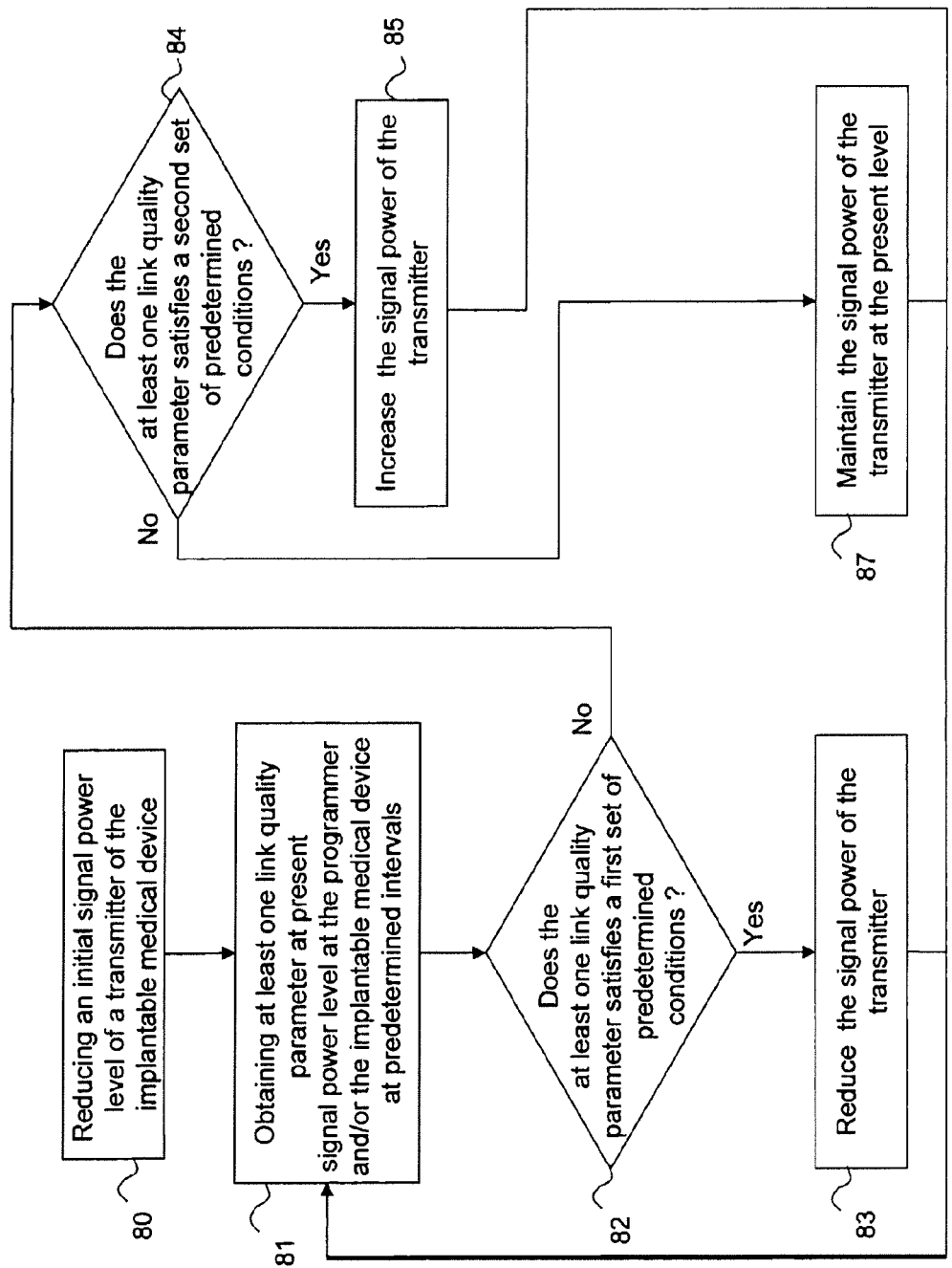
FIG. 8 is a more detailed flow chart illustrating steps of the method for monitoring a link quality and/or link quality margin of a communication link between an implantable medical device and programmer device of a medical system according to the embodiment shown in FIG. 7.

With reference now to FIG. 8, the method for monitoring a link quality and/or link quality margin of a communication link between an implantable medical device and programmer device of a medical system according to an embodiment will be discussed in detail. First, at step 80, the signal power of the transmitter 35 is reduced from an initial signal power according to the signal power adjusting protocol, e.g. a predetermined step. Then, at step 81, at least one link quality parameter at a present signal power level is obtained from a link quality parameter calculation circuit 38 of the implantable medical device 20a and/or from a link quality parameter calculation circuit 15 of the programmer 2b, 2c. This at least one link quality parameter may be obtained at predetermined intervals and in this embodiment the parameters: the number of error corrected blocks (ECC) in the implantable medical device 20a (hereinafter referred to as ECCi), and the number of block that could not be corrected (CRC) in the implantable medical device 20a (hereinafter referred to as CRCi) are obtained. Thereafter, at step 82, it is checked whether ECCi and CRCi, respectively, satisfy a first set of conditions, which in this embodiment are ECCi=0 and CRCi=0 for two consecutive intervals. If yes, the algorithm proceeds to step 83, where the transmitter 35 of the programmer is instructed to reduce the transmitted signal power one step. The step size is determined by, inter alia, the signal power adjusting protocol, and the present signal power. The reduction of the signal power according to the adjusting protocol may be performed in uniform steps or according to successive decreasing steps, i.e. the lower the signal power becomes, the smaller the steps will be. On the other hand, if no, the algorithm proceeds to step 84, where it is checked whether ECCi and CRCi satisfies a second set of conditions, which in this embodiment are ECCi>0 and 0<CRCi<=40. If yes, the algorithm proceeds to step 85, where the where the transmitter 35 of the programmer is instructed to increase the transmitted signal power one step. In one embodiment, the signal power is increased to the preceding higher signal power. However, if it is found that the second set of conditions was not satisfied, the algorithm proceeds to step 87, where the signal power is maintained at the present level.

In a further embodiment of the present invention, the signal power of the transmitter is increased or returned to the initial or maximum power if a fourth set of predetermined conditions are satisfied, which in this embodiment is at an antenna switch or when CRCi>40.

Figure 9:
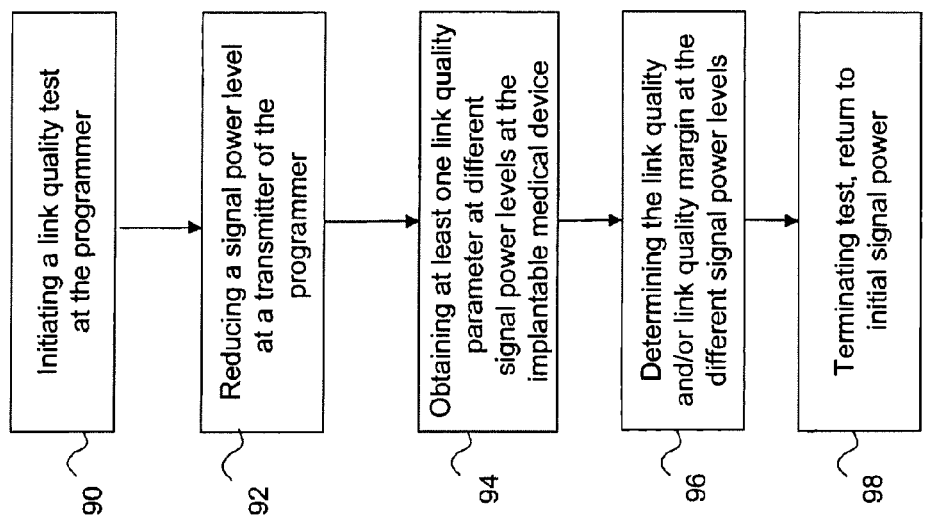
FIG. 9 is a high-level flow chart of an embodiment of the method for determining a link quality and/or link quality margin of a communication link between an implantable medical device and a programmer device of a medical system.

With reference to FIG. 9, a description of the steps of a further embodiment of the method for determining a link quality and/or link quality margin of a communication link between an implantable medical device and programmer device of a medical system will be given. According to this embodiment, the programmer 2, 2a, or 2b or the link quality monitoring circuit 14, initiates the test and determines the link quality and/or link quality margin of the downlink, i.e. from the programmer device 2, 2a, or 2b to the implantable medical device 20. First, at step 90, a link quality test to determine a link quality of a communication link during a communication session between a programmer, for example, the programmer device 2, 2a, or 2b, and the implantable medical device 20 is initiated. As discussed above, the test may be initiated prior to a transmission of data determined to be critical, i.e. after the communication link has been established and at the beginning of the communication session between the programmer device 2, 2a, or 2b and the implantable medical device 20. Alternatively, the test is performed at periodic intervals during normal communication. In one embodiment, a predetermined number of tests are executed and a link quality using the link qualities of the predetermined number of tests is determined.

Then, at step 92, a signal power level of the transmitter 10 of the communication unit 5, 5a of the programmer 2, 2a, or 2b is reduced from an initial signal power level according to a predetermined test protocol. Thereafter, at step 94, at least one link quality parameter is obtained from the link quality parameter calculating circuit 38 of the implantable medical device 20 at reduced signal power. As will be discussed below, the link quality parameters can be obtained in accordance to different test protocols, for example, at each stepwise reduction and/or increment of the signal power or at predetermined interval if the signal power is continuously reduced. In one embodiment, the signal strength, or signal-to-noise ratio (SNR) is obtained as link quality parameters. According to embodiments, at least one of the following parameters are obtained: forward error correction (FEC), cyclic redundancy check (CRC), bit error rate (BER), signal strength, or signal-to-noise ratio (SNR), a link delay of the communication link, a number of re-transmissions of at least one data packet.

Subsequently, at step 96, a present link quality and/or link quality margin is/are determined at reduced signal power using the obtained at least one link quality parameter in the link quality monitoring circuit 14. In one embodiment, the signal strength at the receiver 36 of the implantable medical device 20 is compared with a predetermined signal strength threshold and if the signal strength of the receiver 36 is found to exceed the signal strength threshold, it is determined that the present link quality satisfies predetermined conditions. The link margin may also, or alternatively, be determined by comparing the obtained present signal strength with the predetermined signal strength threshold. As discussed above, the link quality may be determined at each reduced signal power level or at predetermined intervals if the signal power is reduced continuously. Finally, at step 98, when the test is finished, the link quality monitoring circuit 14 instructs the transmitter 10 to return to the initial signal power level.

Figure 10:
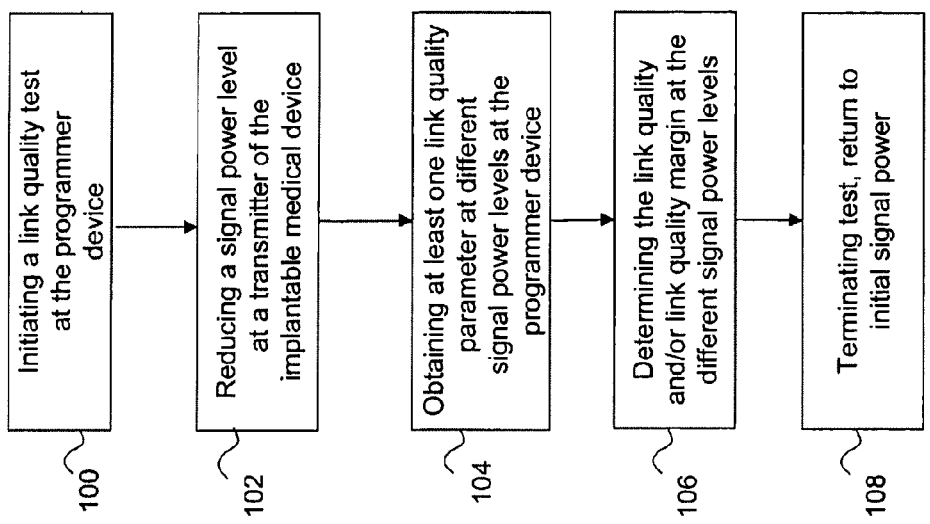
FIG. 10 is a high-level flow chart of another embodiment of the method for determining a link quality and/or link quality margin of a communication link between an implantable medical device and a programmer device of a medical system.

Turning now to FIG. 10, a high-level description of the steps of a further embodiment of the method for determining a link quality and/or link quality margin of a communication link between an implantable medical device and programmer device of a medical system will be given. According to this embodiment, the programmer 2b sends, at step 100, a link quality test instruction via the communication unit 5a to a control circuit or controller 27 of the implantable medical device 20 instructing the control circuit 27 to determine a link quality and/or link quality margin of the uplink of a communication link between the programmer 2b and the implantable medical device 20. The test may be initiated prior to a transmission of data determined to be critical, i.e. after the communication link has been established and at the beginning of the communication session between the programmer device 2b and the implantable medical device 20, or, alternatively, the test is performed at periodic intervals during normal communication. In one embodiment, a predetermined number of tests are executed and a link quality using the link qualities of the predetermined number of tests is determined.

Thereafter, at step 102, a present signal power of the transmitter 35 of the implantable medical device 20 is reduced from an initial signal power level according to a predetermined test protocol. Then, at step 104, at least one link quality parameter at reduced signal power is obtained from a link quality parameter calculation circuit 15 of the programmer 2b. As will be discussed below, the link quality parameters can be obtained in accordance to different test protocols, for example, at each stepwise reduction and/or increment of the signal power or at predetermined interval if the signal power is continuously reduced. In one embodiment, the signal strength, or signal-to-noise ratio (SNR) is obtained as link quality parameters. According to embodiments, at least one of the following parameters are obtained: forward error correction (FEC), cyclic redundancy check (CRC), bit error rate (BER), signal strength, or signal-to-noise ratio (SNR), a link delay of the communication link, a number of re-transmissions of at least one data packet.

Subsequently, at step 106, a present link quality and/or link quality margin at reduced signal power using the obtained at least one link quality parameter is determined in the link quality monitoring circuit 14. In one embodiment, the signal strength at the receiver 12 of the programmer device 2b is compared with a predetermined signal strength threshold and if the signal strength of the receiver is found to exceed the signal strength threshold, it is determined that the present link quality satisfies predetermined conditions. The link margin may also, or alternatively, be determined by comparing the obtained present signal strength with the predetermined signal strength threshold. As discussed above, the link quality may be determined at each reduced signal power level or at predetermined intervals if the signal power is reduced continuously. Finally, at step 108, when the test has been finished, the link quality monitoring circuit 14 sends, via the communication unit 5a, a stop instruction to the control circuit 27 of the implantable medical circuit 20 instructing the control circuit 27 to instruct the transmitter 35 of the implantable medical device 20 to return to the initial signal power.

Figure 11:
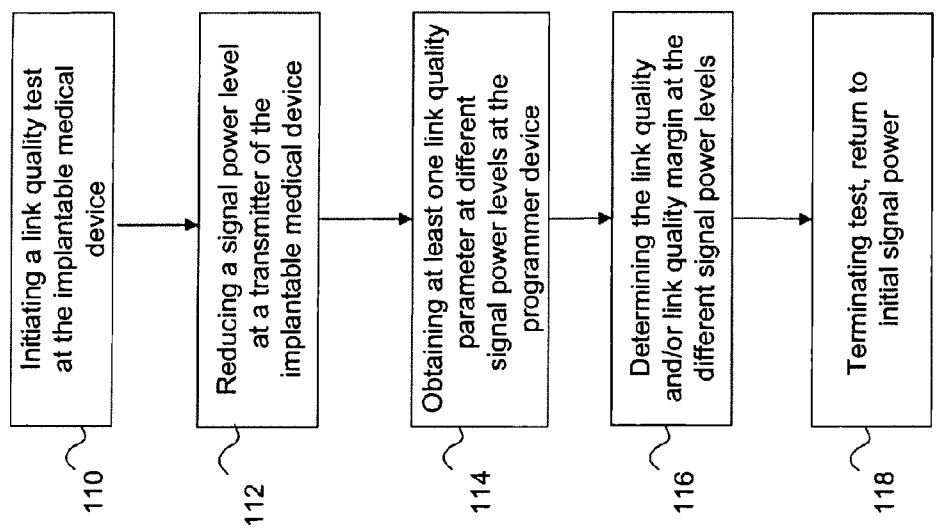
FIG. 11 is a high-level flow chart of a further embodiment of the method for determining a link quality and/or link quality margin of a communication link between an implantable medical device and programmer device of a medical system.

Referring now to FIG. 11, a high-level description of the steps of a further embodiment of the method for determining a link quality and/or link quality margin of a communication link between an implantable medical device and programmer device of a medical system will be given. According to this embodiment, the implantable medical device 20a, or the link quality monitoring circuit 39 of the implantable medical device 20a, initiates the test and determines the link quality and/or link quality margin of the link uplink, i.e. from the implantable medical device 20a to the programmer device 2b, 2d.

First, at step 110, a link quality test to determine a link quality of a communication link during a communication session between the programmer, for example, the programmer device 2b, 2c, and the implantable medical device, for example, the implantable medical device 20a is initiated. As discussed above, the test may be initiated prior to a transmission of data determined to be critical, i.e. after the communication link has been established and at the beginning of the communication session between the programmer device 2b, 2c and the implantable medical device 20a. Alternatively, the test is performed at periodic intervals during normal communication. In one embodiment, a predetermined number of tests are executed and a link quality using the link qualities of the predetermined number of tests is determined.

Then, at step 112, a signal power level of the transmitter 35 of the communication unit 34 of the implantable medical device 20a is reduced from an initial signal power level according to a predetermined test protocol. Thereafter, at step 94, at least one link quality parameter is obtained from the link quality parameter calculating circuit 15 of the programmer device 2b, 2c at reduced signal power. As will be discussed below, the link quality parameters can be obtained in accordance to different test protocols, for example, at each stepwise reduction and/or increment of the signal power or at predetermined interval if the signal power is continuously reduced. In one embodiment, the signal strength, and/or signal-to-noise ratio (SNR) are obtained as link quality parameters. According to embodiments, at least one of the following parameters are obtained: forward error correction (FEC), cyclic redundancy check (CRC), bit error rate (BER), signal strength, or signal-to-noise ratio (SNR), a link delay of the communication link, a number of re-transmissions of at least one data packet.

Subsequently, at step 116, a present link quality and/or link quality margin at reduced signal power using the obtained at least one link quality parameter is determined in the link quality monitoring circuit 39. In one embodiment, the signal strength at the receiver 12 of the programmer device 20a is compared with a predetermined signal strength threshold and if the signal strength of the receiver 12 is found to exceed the signal strength threshold, it is determined that the present link quality satisfies predetermined conditions. The link margin may also, or alternatively, be determined by comparing the obtained present signal strength with the predetermined signal strength threshold. As discussed above, the link quality may be determined at each reduced signal power level or at predetermined intervals if the signal power is reduced continuously. Finally, at step 118, when the test is finished, the controller 27 or the link quality monitoring circuit 39 instructs the transmitter 35 to return to the initial signal power level.

With respect now to FIGS. 12, 13, 14, and 15, tests procedures in accordance with embodiment of the present invention will be discussed. The test procedures will be described with reference to an embodiment where the link quality monitoring circuit 14 is arranged in the programmer device 2, 2a, 2b, the downlink is tested and the at least one link quality parameter is obtained from the implantable medical device 20. In this exemplifying case, the link quality parameter is the signal strength.

Figure 12:
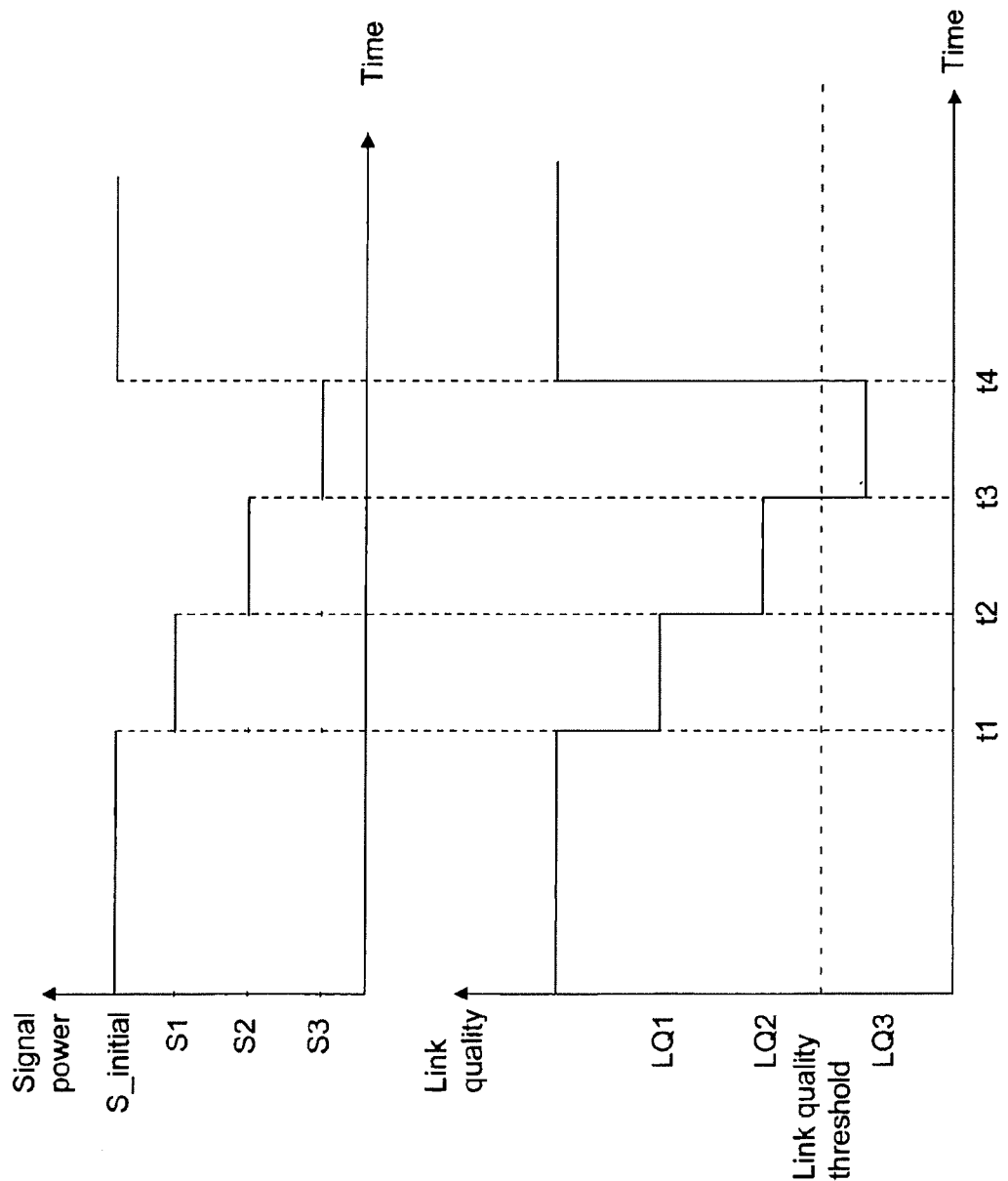
FIG. 12 shows diagrams illustrating the signal power at a transmitter at the programmer and corresponding link quality and link quality margin during a test procedure in accordance with an embodiment of the present invention.
Figure 13:
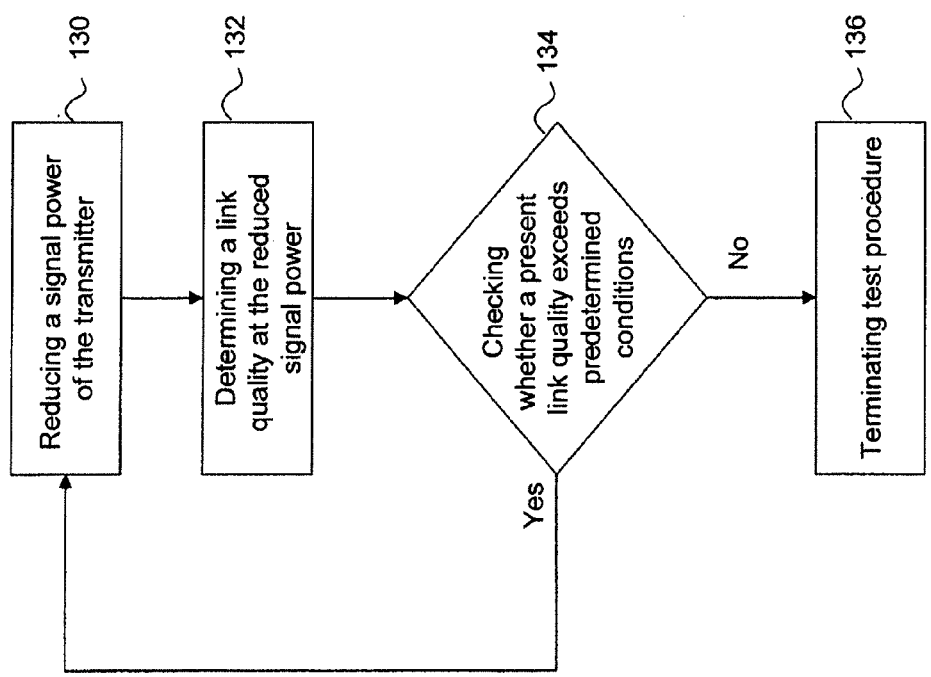
FIG. 13 is flow chart of the embodiment of the method for determining a link quality and/or link quality margin of a communication link between an implantable medical device and programmer device of a medical system including the test procedure shown in FIG. 12.

First, referring to FIGS. 12 and 13, an embodiment where the signal power is reduced step-wise will be discussed. Initially, at step 130, the signal power is reduced from an initial signal power S_initial to a first test signal power S1 at a point of time t1. As can be seen in FIG. 12, the signal power of the transmitter 10 is reduced stepwise at regular intervals, which is performed in accordance with a predetermined test protocol including the step size and the time intervals. Then, at step 132, the link quality is determined at this reduced signal power S1. Thereafter, at step 134, the present link quality is compared with predetermined conditions, which, in one embodiment, is a predetermined link quality threshold and it is determined whether the present link quality exceeds the threshold. If the link quality exceeds the threshold, the link quality is determined to be adequate and the algorithm returns to step 130 where the signal power is reduced a further step, from S1 to S2 at the point of time t2. This procedure is repeated until, at step 134, it is determined that the present link quality is not adequate, i.e. is below the predetermined threshold. In this exemplifying case, the link quality is determined to be adequate at t2 and t3, i.e. the signal strength exceeds the predetermined threshold. At t4, the present link quality is below the threshold and the algorithm proceeds to step 136 where the test is terminated and the signal power is returned to the initial level. The link quality at the initial signal power may be determined when the signal power has returned to the initial level or before the initial signal power has been reduced at the beginning of the test. The link quality margin may also be determined.

In one embodiment, the link quality margin is determined as the difference between the signal strength at the initial signal power and the signal strength being below the threshold. In another embodiment of the present invention, the link quality margin is determined as the difference between the signal strength at the initial signal power and the signal strength at the preceding signal power level. As will be discussed below, the link quality and/or link quality margin may be indicated or presented for a used using, for example, light emitting diodes arranged at the programmer device 2, 2a, 2b, or 2c, and/or at the communication unit 5, 5a. Alternative, the link quality and/or link quality margin may be presented at a display means 8 of programmer 2, 2a, 2b, or 2c using a graphical user interface. The link quality margin may also be determined by using this comparison.

Figure 14:
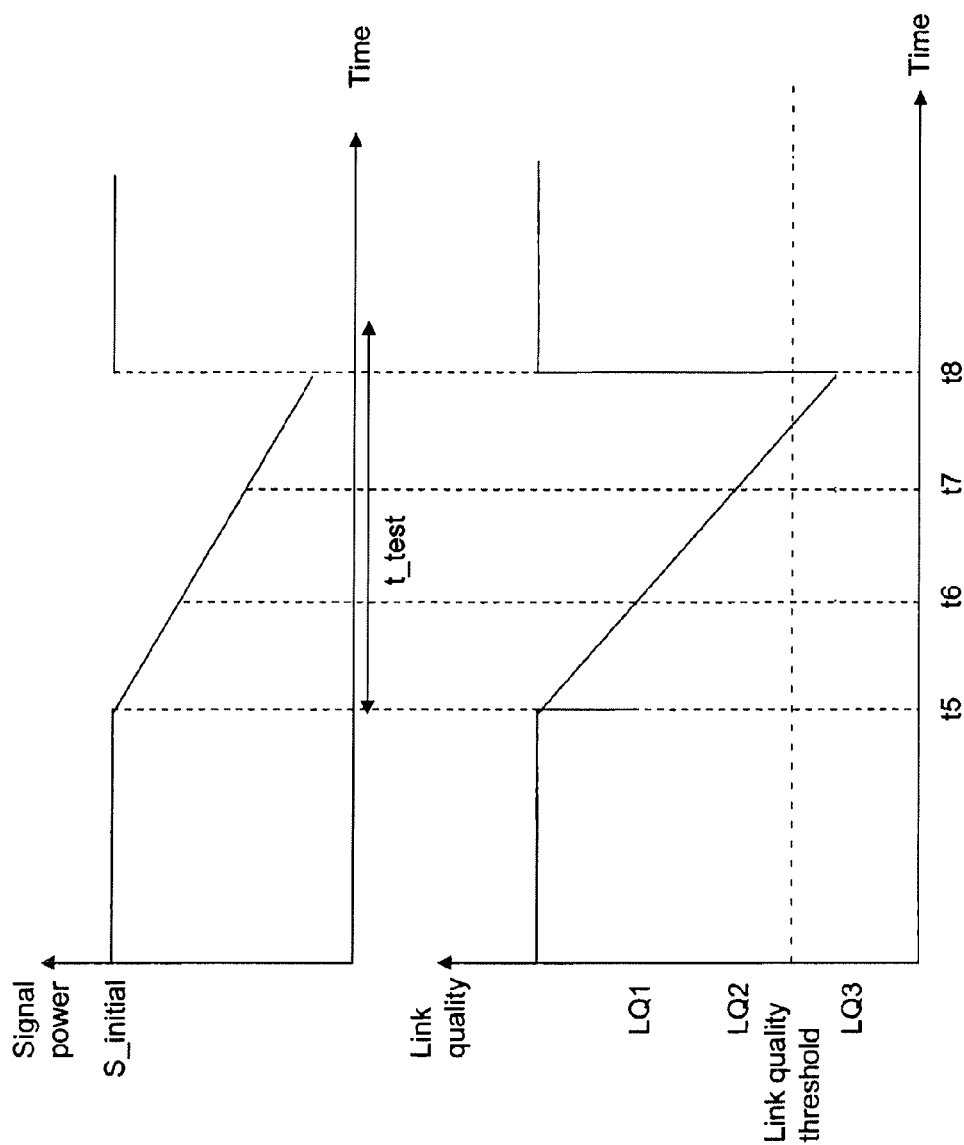
FIG. 14 shows diagrams illustrating the signal power at a transmitter at the programmer and corresponding link quality and link quality margin during a test procedure in accordance with a further embodiment of the present invention.

Referring to FIGS. 14 and 15, an embodiment where the signal power is reduced continuously during a period of time t_test will be discussed.

First, at step 150, the continuous reduction of the signal power from an initial signal power S_initial is initiated. As can be seen in FIG. 14, the signal power of the transmitter 10 is reduced continuously during a test period t_test, which is performed in accordance with a predetermined test protocol including the length of the test period and the reduction rate. Then, at step 152, the link quality is determined after a first time interval t5. Thereafter, at step 154, the present link quality is compared with predetermined conditions, which, in one embodiment, is a predetermined link quality threshold and it is determined whether the present link quality exceeds the threshold. If the link quality exceeds the threshold, the link quality is determined to be adequate and the algorithm returns to step 150 and the reduction of the signal power is continued. This procedure is repeated until, at step 154, it is determined that the present link quality is not adequate, i.e. is below the predetermined threshold. In this exemplifying case, the link quality is determined to be adequate at t6 and t7. At t8, the present link quality is below the threshold and the algorithm proceeds to step 156 where the test is terminated and the signal power is returned to the initial level. The link quality at the initial signal power may be determined when the signal power has returned to the initial level or before the initial signal power has been reduced at the beginning of the test. The link quality margin may also be determined.

In one embodiment, the link quality margin is determined as the difference between the signal strength at the initial signal power and the signal strength being below the threshold. In another embodiment, the link quality margin is determined as the difference between the signal strength at the initial signal power and the signal strength at the preceding signal power level. As will be discussed below, the link quality and/or link quality margin may be indicated or presented for a used using, for example, light emitting diodes arranged at the programmer device 2, 2a, 2b, or 2c, and/or at the communication unit 5, 5a. Alternative, the link quality and/or link quality margin may be presented at a display means 8 of programmer 2, 2a, 2b, or 2c using a graphical user interface. In this illustrated case, the test was terminated before the test period had elapsed since the link quality parameter was found to be below the threshold. According to an alternative, the test can be terminated after the test period has elapsed regardless the level of the link quality.

As discussed above, the link quality and/or link quality margin can be indicated or presented for a user at a display of the programmer device or by means of light emitting means arranged at the programmer device and/or communication unit.

In one embodiment, the determination of whether there is sufficient margin to maintain an adequate RF link is used for the link quality indicator. The link quality indication has two states: link OK and link NOK (not OK). One dual colour LED can be used where the state link OK is indicated with a green light of the LED and the link state link NOK is indicated with a red light. In an alternative embodiment, a single colour LED with different flashing codes are used; where the state link OK is indicates with the LED being continuously lit and the state link NOK is indicated with a flashing light of the LED.

According to another embodiment, the link quality and/link quality margin is indicated with a number of LEDs, for example, five LEDs. A big margin (or a very good link) may be indicated with all five LEDs being lit. Four LEDs are lit when some link margin exists (or when the link is good). Three LEDs are lit when the margin is very little (when the link is OK). Two LEDs are lit when the link margin is below predetermined conditions (the link is degraded). One LED is lit when the far below predetermined conditions (the link is very degraded).

In another embodiment of the present invention, the link quality and/or link quality margin is determined by means of the following parameters: forward error correction, cyclic redundancy check, the number of re-transmissions, the signal strength and the link delay. In this case, five LEDs are used at the programmer and five LEDs at the communication unit. Each LED has a set of limit parameter values, one value for each link quality parameter. As long as all parameters exceed respective limit, the LED is lit. As soon as at least one of the parameters is below the respective limit, the LED will be switched off. The limit values may be chosen so that a big margin (or a very good link) is indicated with all five LEDs being lit. Four LEDs are lit when some link margin exists (or when the link is good). Three LEDs are lit when the margin is very little (when the link is OK). Two LEDs are lit when the link margin is below predetermined conditions (the link is degraded). One LED is lit when the far below predetermined conditions (the link is very degraded).

According to yet another embodiment of the present invention, link quality and/or the link quality margin is presented in a visually recognizable way for an operator by means of at least one distinctive colour and at least one distinctive symbol at a display screen 8, wherein a control circuit 4 of the programmer device 2, 2a, 2b, or 2d comprises means for generating a graphical user interface on the display screen adapted to present the symbol (-s) and/or the distinctive colour. For example, a green and positive symbol (e.g. a star or a shining sun) may indicate a big margin, a yellow question mark may indicate a small margin, and a red cross may indicate a "negative margin" (i.e. a present link quality below the threshold).

In a certain embodiment, the green and positive symbol may indicate a transmission condition where all data is transmitted without errors (e.g. ECCi=0 and CRCi=0), the a yellow question mark may indicate that data is transmitted, but error corrections and retransmissions are necessary and the data is transmitted correctly despite errors and corrections in the received signals (e.g. ECCi>0 and 0<CRCi<=40), and a red cross may indicate that the received data contains too much errors to allow a reconstruction of the information (e.g. CRCi>40).

The preceding specific embodiments are illustrative of the practice of the invention. It is to be understood, therefore, that other expedients known to those of skill in the art or disclosed herein may be employed without departing from the invention as defined by the appended claims. It is therefore understood that the invention may be practiced otherwise than is specifically described without departing from the scope of the present invention.

The invention claimed is:

1. A medical system comprising:
    an implantable medical device configured for implantation in a subject, said implantable medical device comprising a receiver;
    an external programmer device configured for extracorporeal communication with said implantable medical device in the subject, said external programmer device comprising a transmitter that establishes a wireless communication link with said receiver of said implantable medical device;
    a link quality monitoring circuit in said external programmer configured to determine a link quality of said communication link during a communication session between said external programmer device and said implantable medical device;

a link quality parameter calculation unit, located in either said external programmer or said implantable medical device, configured to calculate a link quality parameter that represents a quality of said communication link in said communication session; and said link quality monitoring circuit being configured to instruct said transmitter of said external programmer to reduce a signal power of a signal transmitted to said receiver from an initial signal power level according to a predetermined signal power adjusting protocol, and to obtain said link quality parameter from said link quality parameter calculation unit, and to determine a present link quality using said at least one link quality parameter, and to instruct said transmitter to adjust the reduced signal power level dependent on said present link quality and said signal power adjusting protocol, and to instruct said transmitter to return to said initial signal power level if said link quality parameter satisfies a first set of predetermined conditions.

2. A medical system as claimed in claim 1 wherein said link quality monitoring circuit is configured to instruct said transmitter to reduce said signal power level from said present signal power level according to said signal power adjusting protocol, if said link quality parameter satisfies a second set of predetermined conditions, and to instruct said transmitter to increase said signal power level from said present signal power level according to said signal power adjusting protocol, if said link quality parameter satisfies a third set of predetermined conditions.

3. A medical system as claimed in claim 2 wherein said link quality monitoring circuit is configured to instruct said transmitter to maintain said present signal power level at said present signal power level if said link quality parameters satisfies a fourth set of predetermined conditions.

4. A medical system as claimed in claim 3 wherein said transmitter is configured to transmit data in blocks, and wherein said external programmer device comprises an antenna connected to said transmitter that transmits said data in said blocks to said receiver of said implantable medical device, and wherein said first set of conditions comprises a number of said blocks containing errors that could not be corrected in said implantable medical device (CRCi) being higher than 40, or a change of said antenna of said external programmer device, and wherein said second set of conditions comprises a number of error corrected blocks in said implantable medical device (ECCi) being equal to zero and CRCi being equal to zero for two consecutive determinations of said link quality parameter, and wherein said third set of conditions comprises ECCi being higher than 10 and CRCi being higher than zero and lower than 40, and wherein said fourth set of conditions comprises ECCi being lower than 10 and CRCi being equal to or greater than zero and less than 40.

5. A medical system as claimed in claim 1 wherein said link quality monitoring circuit is configured to determine said link quality in a link quality test, and to instruct said transmitter to return to said initial signal power level when said link quality test is concluded.

6. A system as claimed in claim 1 wherein said link quality parameter calculation unit calculates said link quality parameter from the group of link quality parameters consisting of signal strength and signal-to-noise ratio.

7. A system as claimed in claim 1 wherein said implantable medical device comprises a transmitter that transmits a response signal upon said receiver of said implantable medical device receiving the signal transmitted from said transmitter of said external programmer device, and wherein said link quality parameter calculation unit is configured to calculate a link delay of said communication link dependent on a response received by said external programmer device following transmission of a signal from said external programmer device to said implantable medical device, or to read a register in said external programmer device.

8. A system as claimed in claim 1 wherein said transmitter is configured to transmit data to said implantable medical device, and wherein said monitoring unit is configured to identify when data to be transmitted by said transmitter are critical data, and to initiate a link quality test, wherein said link quality is determined, prior to transmission of said data classified as critical.

9. A system as claimed in claim 1 wherein said programmer device comprises a presentation unit configured to provide a visual indication of said link quality or a link quality margin.

10. A system as claimed in claim 9 wherein said presentation unit comprises two light emitting diodes operable by said link quality monitoring circuit to provide a visual indication of said link quality or said link quality margin.

11. A system as claimed in claim 9 wherein said presentation unit is a display screen, and wherein said programmer device comprises a control unit control unit connected to said display screen that generates a graphical user interface at said display screen that is a visual indicator of said link quality or said link quality margin.

12. A system as claimed in claim 9 wherein said link quality monitoring circuit is configured to determine a quality level of said link quality or said link quality margin, wherein a first quality level represents a link quality above a predetermined upper level above a threshold, a second quality level represents a link quality between said predetermined upper level and said threshold, and a third quality level represents a link quality below said threshold, and wherein said presentation unit comprises a display screen, and wherein said programmer device comprises a control circuit connected to said display screen, said control circuit being configured to generate a graphical user interface at said display screen that indicates said first quality level with a first color and a first symbol, and that indicates said second quality level with a second color and a second symbol, and that indicates said third quality level with a third color and a third symbol.

13. A medical system comprising:

an implantable medical device configured for implantation in a subject, said implantable medical device comprising a transmitter;

an external programmer device configured for extracorporeal communication with said implantable medical device in the subject, said external programmer device comprising a receiver, and said transmitter in said implantable medical device being configured to establish a wireless communication link with said receiver of said external programmer;

a link quality monitoring circuit in said implantable medical device configured to determine a link quality of said communication link during a communication session between said external programmer and said implantable medical device;

a link quality parameter calculation unit, located in either said external programmer or said implantable medical device, configured to calculate a link quality parameter that represents a quality of said communication link in said communication session; and said link quality monitoring circuit being configured to instruct said transmitter of said implantable medical device to reduce a signal power of a signal transmitted to said receiver from an initial signal power level according to a predetermined signal power adjusting protocol, and to obtain said link quality parameter from said link quality parameter calculation unit, and to determine a present link quality using said at least one link quality parameter, and to instruct said transmitter to adjust the reduced signal power level dependent on said present link quality and said signal power adjusting protocol, and to instruct said transmitter to return to said initial signal power level if said link quality parameter satisfies a first set of predetermined conditions.

14. A medical system as claimed in claim 13 wherein said link quality monitoring circuit is configured to instruct said transmitter to reduce said signal power level from said present signal power level according to said signal power adjusting protocol, if said link quality parameter satisfies a second set of predetermined conditions, and to instruct said transmitter to increase said signal power level from said present signal power level according to said signal power adjusting protocol, if said link quality parameter satisfies a third set of predetermined conditions.

15. A medical system as claimed in claim 14 wherein said link quality monitoring circuit is configured to instruct said transmitter to maintain said present signal power level at said present signal power level if said link quality parameters satisfies a fourth set of predetermined conditions.

16. A medical system as claimed in claim 15 wherein said transmitter is configured to transmit data in blocks, and wherein said implantable medical device comprises an antenna connected to said transmitter that transmits said data in said blocks to said receiver of said external programmer device, and wherein said first set of conditions comprises a number of said blocks containing errors that could not be corrected in said implantable medical device (CRCi) being higher than 40, or a change of said antenna of said implantable medical device, and wherein said second set of conditions comprises a number of error corrected blocks in said implantable medical device (ECCi) being equal to zero and CRCi being equal to zero for two consecutive determinations of said link quality parameter, and wherein said third set of conditions comprises ECCi being higher than 10 and CRCi being higher than zero and lower than 40, and wherein said fourth set of conditions comprises ECCi being lower than 10 and CRCi being equal to or greater than zero and less than 40.

17. A medical system as claimed in claim 13 wherein said link quality monitoring circuit is configured to determine said link quality in a link quality test, and to instruct said transmitter to return to said initial signal power level when said link quality test is concluded.

18. A system as claimed in claim 13 wherein said link quality parameter calculation unit calculates said link quality parameter from the group of link quality parameters consisting of signal strength and signal-to-noise ratio.

19. A system as claimed in claim 13 wherein said external programmer device comprises a transmitter that transmits a response signal upon said receiver of said external programmer device receiving the signal transmitted from said transmitter of said implantable medical device, and wherein said link quality parameter calculation unit is configured to calculate a link delay of said communication link dependent on a response received by said implantable medical device following transmission of a signal from said implantable medical device to said external programmer device, or to read a register in said implantable medical device.

20. A system as claimed in claim 13 wherein said transmitter is configured to transmit data to said external programmer device, and wherein said monitoring unit is configured to identify when data to be transmitted by said transmitter are critical data, and to initiate a link quality test, wherein said link quality is determined, prior to transmission of said data classified as critical.

21. A system as claimed in claim 13 wherein said programmer device comprises a presentation unit configured to provide a visual indication of said link quality or a link quality margin.

22. A system as claimed in claim 21 wherein said presentation unit comprises two light emitting diodes operable by said link quality monitoring circuit to provide a visual indication of said link quality or said link quality margin.

23. A system as claimed in claim 21 wherein said presentation unit is a display screen, and wherein said programmer device comprises a control unit control unit connected to said display screen that generates a graphical user interface at said display screen that is a visual indicator of said link quality or said link quality margin.

24. A system as claimed in claim 21 wherein said link quality monitoring circuit is configured to determine a quality level of said link quality or said link quality margin, wherein a first quality level represents a link quality above a predetermined upper level above a threshold, a second quality level represents a link quality between said predetermined upper level and said threshold, and a third quality level represents a link quality below said threshold, and wherein said presentation unit comprises a display screen, and wherein said programmer device comprises a control circuit connected to said display screen, said control circuit being configured to generate a graphical user interface at said display screen that indicates said first quality level with a first color and a first symbol, and that indicates said second quality level with a second color and a second symbol, and that indicates said third quality level with a third color and a third symbol.

25. A method for operating a medical system comprising an implantable medical device configured for implantation in a subject, said implantable medical device comprising a receiver, and an external programmer device configured for extracorporeal communication with said implantable medical device in the subject, said external programmer device comprising a transmitter, said method comprising the steps of:
  establishing a wireless communication link between said transmitter of said external programmer device and with said receiver of said implantable medical device;
  in a link quality monitoring circuit in said external programmer, automatically determining a link quality of said communication link during a communication session between said external programmer device and said implantable medical device;
  in a link quality parameter calculation unit, located in either said external programmer or said implantable medical device, automatically calculating a link quality parameter that represents a quality of said communication link in said communication session; and
  from said link quality monitoring circuit, automatically instructing said transmitter of said external programmer device to reduce a signal power of a signal transmitted to said receiver from an initial signal power level according to a predetermined signal power adjusting protocol, and to obtain said link quality parameter from said link quality parameter calculation unit, and to determine a present link quality using said at least one link quality parameter, and to instruct said transmitter to adjust the reduced signal power level dependent on said present link quality and said signal power adjusting protocol, and to instruct said transmitter to return to said initial signal power level if said link quality parameter satisfies a first set of predetermined conditions.

26. A method as claimed in claim 25 comprising, from said link quality monitoring circuit, instructing said transmitter to reduce said signal power level from said present signal power level according to said signal power adjusting protocol, if said link quality parameter satisfies a second set of predetermined conditions, and to instruct said transmitter to increase said signal power level from said present signal power level according to said signal power adjusting protocol, if said link quality parameter satisfies a third set of predetermined conditions.

27. A method as claimed in claim 26 comprising, from said link quality monitoring circuit, instructing said transmitter to maintain said present signal power level at said present signal power level if said link quality parameters satisfies a fourth set of predetermined conditions.

28. A method for operating a medical system comprising an implantable medical device configured for implantation in a subject, said implantable medical device comprising a transmitter and an external programmer device configured for extracorporeal communication with said implantable medical device in the subject, said external programmer device comprising a receiver, said method comprising the steps of:

establishing a wireless communication link between said receiver of said external programmer device and said transmitter of said implantable medical device;

in a link quality monitoring circuit in said implantable medical device, automatically determining a link quality of said communication link during a communication session between said external programmer device and said implantable medical device;

in a link quality parameter calculation unit, located in either said external programmer or said implantable medical device, automatically calculating a link quality parameter that represents a quality of said communication link in said communication session; and from said link quality monitoring circuit, instructing said transmitter of said implantable medical device to reduce a signal power of a signal transmitted to said receiver from an initial signal power level according to a predetermined signal power adjusting protocol, and to obtain said link quality parameter from said link quality parameter calculation unit, and to determine a present link quality using said at least one link quality parameter, and to instruct said transmitter to adjust the reduced signal power level dependent on said present link quality and said signal power adjusting protocol, and to instruct said transmitter to return to said initial signal power level if said link quality parameter satisfies a first set of predetermined conditions.

* * * * *